United States Patent
Albrecht et al.

(10) Patent No.: US 9,259,238 B2
(45) Date of Patent: *Feb. 16, 2016

(54) BALLOON TROCAR

(71) Applicant: Applied Medical Resources Corporation, Rancho Santa Margarita, CA (US)

(72) Inventors: Jeremy J. Albrecht, Rancho Santa Margarita, CA (US); Gigi Au, Anaheim, CA (US); Eric Nguyen, Rancho Santa Margarita, CA (US); Donald L. Gadberry, Capistrano Beach, CA (US); John R. Brustad, Rancho Santa Margarita, CA (US); Gary M. Johnson, Rancho Santa Margarita, CA (US); Charles C. Hart, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,536

(22) Filed: Jan. 26, 2015

(65) Prior Publication Data

US 2015/0141916 A1    May 21, 2015

Related U.S. Application Data

(63) Continuation of application No. 13/438,566, filed on Apr. 3, 2012, now Pat. No. 8,939,946, which is a continuation of application No. 11/374,188, filed on Mar. 13, 2006, now Pat. No. 8,147,453.

(51) Int. Cl.
*A61M 5/00* (2006.01)
*A61B 17/34* (2006.01)
(Continued)

(52) U.S. Cl.
CPC ......... *A61B 17/3417* (2013.01); *A61B 17/3415* (2013.01); *A61B 17/3421* (2013.01);
(Continued)

(58) Field of Classification Search
CPC .............. A61B 2017/349; A61B 2017/22051; A61B 17/3415; A61B 17/3423; A61B 17/3417; A61B 17/3421; A61B 2017/3419; A61B 2017/00557; A61B 2017/3433; A61B 2017/3445; A61B 2017/3486; A61B 2017/3488; A61M 2039/0261; A61M 2039/0273; A61M 2039/0279; A61M 2039/0294; A61M 2039/0223; A61M 2039/0229; A61M 2039/0232; A61M 2039/0626; A61M 39/0247; A61M 39/06

See application file for complete search history.

(56) References Cited

U.S. PATENT DOCUMENTS 2,185,927 A   2/1940   Shelanski
2,687,131 A   8/1954   Raiche
(Continued)

FOREIGN PATENT DOCUMENTS

EP   0 530 595   3/1993
EP   1 097 675   5/2001
(Continued)

OTHER PUBLICATIONS

The International Bureau of WIPO, International Preliminary Report on Patentability for International Application No. PCT/US2008/053298 mailed Sep. 17, 2009.

(Continued)

*Primary Examiner* — Bhisma Mehta
*Assistant Examiner* — Jenna Zhang
(74) *Attorney, Agent, or Firm* — John F. Heal

(57) ABSTRACT

A balloon trocar includes a cannula assembly including a cannula and an outer sleeve fitting over the cannula. The distal end of the outer sleeve is proximal to the distal end of the cannula. A balloon is coupled to a distal portion of the sleeve and a distal portion of the cannula. The outer surface of the cannula includes a plurality of longitudinal channels for transmitting gas or fluid to the balloon. A bolster having a gel pad at its distal portion is slidably mounted to the cannula assembly and may be locked in a desired position. In use, the trocar is inserted into an incision through a body wall and into a body cavity. The balloon is inflated and the cannula assembly pulled proximally against the incision while the bolster is slid distally to the body wall and locked in place to seal the incision with the compressed balloon.

19 Claims, 23 Drawing Sheets

(51) Int. Cl.
  *A61M 39/02* (2006.01)
  *A61M 39/06* (2006.01)
  *A61M 29/00* (2006.01)
  *A61B 17/22* (2006.01)
  *A61M 25/04* (2006.01)
  *A61J 15/00* (2006.01)
  *A61B 17/02* (2006.01)
  *A61B 17/00* (2006.01)

(52) U.S. Cl.
  CPC ........... *A61M39/0247* (2013.01); *A61M 39/06* (2013.01); *A61B 17/0218* (2013.01); *A61B 17/3423* (2013.01); *A61B 17/3498* (2013.01); *A61B 2017/00477* (2013.01); *A61B 2017/00557* (2013.01); *A61B 2017/22051* (2013.01); *A61B 2017/347* (2013.01); *A61B 2017/349* (2013.01); *A61B 2017/3419* (2013.01); *A61B 2017/3433* (2013.01); *A61B 2017/3445* (2013.01); *A61B 2017/3486* (2013.01); *A61B 2017/3488* (2013.01); *A61J 15/0053* (2013.01); *A61M 25/04* (2013.01); *A61M 2039/0261* (2013.01); *A61M 2039/0273* (2013.01); *A61M 2039/0279* (2013.01); *A61M 2039/0294* (2013.01); *A61M 2039/062* (2013.01); *A61M 2039/0626* (2013.01); *A61M 2039/0686* (2013.01)

(56) References Cited

U.S. PATENT DOCUMENTS

| | | | |
|---|---|---|---|
| 3,039,468 | A | 6/1962 | Price |
| 3,044,468 | A | 7/1962 | Birtwell |
| 3,154,077 | A | 10/1964 | Cannon |
| 3,253,594 | A | 5/1966 | Matthews et al. |
| 3,459,175 | A | 8/1969 | Miller |
| 3,484,121 | A * | 12/1969 | Quinton ................ A61M 39/10 285/242 |
| 3,634,924 | A | 1/1972 | Blake et al. |
| 3,817,251 | A | 6/1974 | Hasson |
| 3,952,742 | A | 4/1976 | Taylor |
| 3,962,519 | A | 6/1976 | Rusch et al. |
| 3,970,090 | A | 7/1976 | Loiacono |
| 3,971,385 | A | 7/1976 | Corbett |
| 4,077,412 | A | 3/1978 | Mossun |
| 4,496,345 | A | 1/1985 | Hasson |
| 4,555,242 | A | 11/1985 | Saudagar |
| 4,601,710 | A | 7/1986 | Moll |
| 4,649,904 | A | 3/1987 | Krauter et al. |
| 4,655,752 | A | 4/1987 | Honkanen et al. |
| 4,670,008 | A | 6/1987 | Von Albertini |
| 4,809,679 | A | 3/1989 | Shimonaka et al. |
| 4,834,721 | A | 5/1989 | Onohara et al. |
| 4,861,334 | A | 8/1989 | Nawaz |
| 4,946,464 | A | 8/1990 | Pevsner |
| 5,002,557 | A * | 3/1991 | Hasson ................ A61B 17/34 604/174 |
| 5,009,643 | A | 4/1991 | Reich et al. |
| 5,098,388 | A | 3/1992 | Kulkashi et al. |
| 5,100,390 | A | 3/1992 | Lubeck et al. |
| 5,103,804 | A | 4/1992 | Abele et al. |
| 5,122,122 | A | 6/1992 | Allgood |
| 5,147,316 | A | 9/1992 | Castillenti |
| 5,176,697 | A | 1/1993 | Hasson et al. |
| 5,203,773 | A | 4/1993 | Green |
| 5,226,890 | A | 7/1993 | Ianniruberto et al. |
| D338,270 | S | 8/1993 | Stephens et al. |
| 5,257,975 | A | 11/1993 | Foshee |
| 5,271,380 | A | 12/1993 | Riek et al. |
| 5,273,545 | A | 12/1993 | Hunt et al. |
| 5,279,567 | A | 1/1994 | Ciaglia et al. |
| 5,290,249 | A | 3/1994 | Foster |
| 5,300,036 | A | 4/1994 | Mueller et al. |
| 5,309,896 | A | 5/1994 | Moll et al. |
| 5,330,497 | A | 7/1994 | Freitas et al. |
| 5,331,975 | A | 7/1994 | Bonutti |
| 5,354,270 | A | 10/1994 | Wilk et al. |
| 5,355,897 | A | 10/1994 | Pietrafitta et al. |
| 5,361,752 | A | 11/1994 | Moll et al. |
| 5,370,134 | A | 12/1994 | Chin et al. |
| D354,562 | S | 1/1995 | Medema |
| 5,383,889 | A | 1/1995 | Warner et al. |
| 5,395,333 | A | 3/1995 | Brill |
| 5,402,772 | A | 4/1995 | Moll et al. |
| 5,403,336 | A | 4/1995 | Kieturakis et al. |
| 5,425,357 | A | 6/1995 | Moll et al. |
| 5,431,173 | A | 7/1995 | Chin et al. |
| 5,437,646 | A | 8/1995 | Hunt et al. |
| 5,445,615 | A | 8/1995 | Yoon |
| 5,445,644 | A | 8/1995 | Pietrafitta et al. |
| 5,450,843 | A | 9/1995 | Moll et al. |
| 5,454,367 | A | 10/1995 | Moll et al. |
| 5,464,449 | A | 11/1995 | Ryan et al. |
| 5,465,711 | A | 11/1995 | Moll et al. |
| 5,468,248 | A | 11/1995 | Chin et al. |
| 5,472,429 | A | 12/1995 | Yoon |
| 5,478,329 | A | 12/1995 | Ternamian |
| 5,496,280 | A * | 3/1996 | Vandenbroek ..... A61B 17/3498 604/167.03 |
| 5,501,653 | A | 3/1996 | Chin |
| 5,503,631 | A | 4/1996 | Onishi et al. |
| 5,505,689 | A | 4/1996 | Kramer et al. |
| 5,512,051 | A | 4/1996 | Wang et al. |
| 5,514,075 | A | 5/1996 | Moll et al. |
| 5,514,096 | A | 5/1996 | Hiejima et al. |
| 5,520,609 | A | 5/1996 | Moll et al. |
| 5,522,790 | A | 6/1996 | Moll et al. |
| 5,527,264 | A | 6/1996 | Moll et al. |
| 5,531,688 | A | 7/1996 | Hiejima et al. |
| 5,531,856 | A | 7/1996 | Moll et al. |
| 5,540,675 | A | 7/1996 | Hassoon |
| 5,562,603 | A | 10/1996 | Moll et al. |
| 5,562,684 | A * | 10/1996 | Kammerer ......... A61B 17/0401 289/17 |
| 5,569,165 | A | 10/1996 | Chin et al. |
| 5,575,759 | A | 11/1996 | Moll et al. |
| 5,591,191 | A | 1/1997 | Kieturakis |
| 5,601,559 | A | 2/1997 | Melker et al. |
| 5,630,805 | A | 5/1997 | Ternamian |
| 5,632,761 | A | 5/1997 | Smith et al. |
| 5,634,883 | A | 6/1997 | Chin et al. |
| 5,643,178 | A | 7/1997 | Moll et al. |
| 5,649,909 | A | 7/1997 | Cornelius |
| 5,656,013 | A | 8/1997 | Yoon |
| 5,658,272 | A | 8/1997 | Hasson |
| 5,676,636 | A | 10/1997 | Chin |
| 5,690,607 | A | 11/1997 | Chin et al. |
| 5,697,913 | A | 12/1997 | Sierocuk et al. |
| 5,704,372 | A | 1/1998 | Moll et al. |
| 5,713,869 | A | 2/1998 | Morejon |
| 5,716,327 | A | 2/1998 | Warner et al. |
| 5,722,983 | A * | 3/1998 | Van Der Weegen ............ A61B 1/00142 606/193 |
| 5,722,986 | A | 3/1998 | Smith et al. |
| 5,728,119 | A | 3/1998 | Smith et al. |
| 5,738,629 | A | 4/1998 | Moll et al. |
| 5,743,850 | A | 4/1998 | Moll et al. |
| 5,743,851 | A | 4/1998 | Moll et al. |
| 5,746,762 | A | 5/1998 | Bass |
| 5,772,632 | A | 6/1998 | Forman |
| 5,779,728 | A | 7/1998 | Lunsford et al. |
| 5,795,332 | A | 8/1998 | Lucas et al. |
| 5,803,901 | A | 9/1998 | Chin et al. |
| 5,820,555 | A | 10/1998 | Watkins et al. |
| 5,830,232 | A | 11/1998 | Hasson |
| 5,836,871 | A | 11/1998 | Wallace et al. |
| 5,836,913 | A | 11/1998 | Orth et al. |
| 5,855,566 | A | 1/1999 | Dunlap |
| 5,865,728 | A | 2/1999 | Moll et al. |
| 5,895,351 | A | 4/1999 | Nottage et al. |
| 5,924,424 | A | 7/1999 | Stevens et al. |
| 5,925,058 | A | 7/1999 | Smith et al. |

(56) References Cited

U.S. PATENT DOCUMENTS

| | | | |
|---|---|---|---|
| 5,935,098 A | 8/1999 | Blaisdell et al. | |
| 5,951,588 A | 9/1999 | Moenning | |
| 5,957,888 A | 9/1999 | Hinchiffe | |
| 5,961,490 A | 10/1999 | Adams | |
| 5,968,065 A | 10/1999 | Chin | |
| 5,984,896 A | 11/1999 | Boyd | |
| 5,993,471 A | 11/1999 | Riza et al. | |
| 6,033,379 A | 3/2000 | Barra et al. | |
| 6,102,928 A | 8/2000 | Bonutti | |
| 6,203,526 B1 | 3/2001 | McBeth et al. | |
| 6,203,558 B1 | 3/2001 | Dusbabek et al. | |
| 6,224,608 B1 | 5/2001 | Ciccolella et al. | |
| 6,238,373 B1 | 5/2001 | De la Torre et al. | |
| 6,264,670 B1 | 7/2001 | Chin | |
| 6,306,144 B1 | 10/2001 | Sydney et al. | |
| 6,344,038 B1 | 2/2002 | Weber | |
| 6,355,029 B1 | 3/2002 | Joye et al. | |
| 6,361,543 B1 | 3/2002 | Chin et al. | |
| 6,432,085 B1 | 8/2002 | Stellon et al. | |
| 6,451,041 B1 | 9/2002 | Moenning et al. | |
| 6,458,138 B1 | 10/2002 | Sydney et al. | |
| 6,485,410 B1 | 11/2002 | Loy | |
| 6,524,283 B1 | 2/2003 | Hopper et al. | |
| 6,589,167 B1 | 7/2003 | Shimomura et al. | |
| 6,605,037 B1 | 8/2003 | Moll et al. | |
| 6,626,918 B1 | 9/2003 | Ginn et al. | |
| 6,632,197 B2 | 10/2003 | Lyon | |
| 6,638,265 B1 | 10/2003 | Ternamian | |
| 6,648,873 B2 | 11/2003 | Arenberg et al. | |
| 6,723,052 B2 * | 4/2004 | Mills | A61B 8/0833 600/420 |
| 6,733,439 B2 | 5/2004 | Zigler | |
| 6,808,492 B2 | 10/2004 | Snyder | |
| 6,811,546 B1 | 11/2004 | Callas et al. | |
| 6,814,713 B2 | 11/2004 | Aboul-Hosn et al. | |
| 6,908,454 B2 | 6/2005 | McFairlane | |
| 6,908,462 B2 | 6/2005 | Joye et al. | |
| 6,923,827 B2 | 8/2005 | Campbell et al. | |
| 7,033,384 B2 | 4/2006 | Gannoe et al. | |
| 7,052,507 B2 | 5/2006 | Wakuda et al. | |
| 7,153,319 B1 | 12/2006 | Haberland et al. | |
| 7,235,064 B2 | 6/2007 | Hopper et al. | |
| 7,300,448 B2 | 11/2007 | Criscuolo et al. | |
| 7,449,011 B2 * | 11/2008 | Wenchell | A61B 17/3421 604/104 |
| 7,691,089 B2 | 4/2010 | Gresham | |
| 2003/0139758 A1 | 7/2003 | Hopper et al. | |
| 2004/0098045 A1 | 5/2004 | Grafton et al. | |
| 2004/0111061 A1 | 6/2004 | Curran | |
| 2004/0116894 A1 | 6/2004 | DeLegge | |
| 2004/0138702 A1 * | 7/2004 | Peartree | A61B 17/3421 606/213 |
| 2005/0004592 A1 | 1/2005 | Criscuolo | |
| 2005/0113856 A1 | 5/2005 | Epstein et al. | |
| 2005/0165432 A1 * | 7/2005 | Heinrich | A61B 17/3417 606/167 |
| 2005/0177104 A1 | 8/2005 | Conway | |
| 2005/0192615 A1 | 9/2005 | Torre et al. | |
| 2005/0209607 A1 | 9/2005 | Lipchitz et al. | |
| 2006/0047293 A1 * | 3/2006 | Haberland | A61B 17/3462 606/167 |
| 2006/0079838 A1 | 4/2006 | Walker et al. | |
| 2006/0079922 A1 | 4/2006 | Creston | |
| 2007/0213675 A1 | 9/2007 | Albrecht et al. | |
| 2007/0225643 A1 * | 9/2007 | Hopper | A61B 17/3421 604/101.01 |
| 2008/0306442 A1 | 12/2008 | Bardsley et al. | |

FOREIGN PATENT DOCUMENTS

| | | |
|---|---|---|
| RU | 2234872 | 8/2004 |
| WO | WO 92/21291 | 12/1992 |
| WO | WO 92/21292 | 12/1992 |
| WO | WO 92/21294 | 12/1992 |
| WO | WO 92/21295 | 12/1992 |
| WO | WO 92/21298 | 12/1992 |
| WO | WO 97/06732 | 2/1997 |
| WO | WO 2004/032756 | 4/2004 |
| WO | WO 2004/047656 | 6/2004 |

OTHER PUBLICATIONS

The International Bureau of WIPO, International Preliminary Report on Patentability for International Application No. PCT/US2007/063728 dated Sep. 16, 2008.

European Patent Office, Written Opinion of the International Searching Authority and International Search Report for International Application No. PCT/US2007/063728, mailed Sep. 4, 2007.

International Searching Authority (US), The International Search Report and the Written Opinion of the International Searching Authority, for International Application No. PCT/US08/53298, mailed Aug. 19, 2008.

* cited by examiner

BALLOON TROCAR

CROSS-REFERENCE TO RELATED APPLICATION

This application is a continuation of U.S. patent application Ser. No. 13/438,566, entitled "Balloon Trocar," filed on Apr. 3, 2012, currently pending, which is a continuation of U.S. patent application Ser. No. 11/374,188 entitled "Balloon Trocar," filed on Mar. 13, 2006, which issued as U.S. Pat. No. 8,147,453, each of which is fully incorporated herein by reference.

BACKGROUND

This invention relates generally to trocar systems including cannulas and, more specifically, to trocars having a balloon retention device.

Trocar systems have been of particular advantage in facilitating less invasive surgery across a body wall and within a body cavity. This is particularly true in abdominal surgery where trocars have provided a working channel across the abdominal wall to facilitate the use of instruments within the abdominal cavity.

Trocar systems typically include a cannula, which provides the working channel, and an obturator that is used to place the cannula across a body wall, such as the abdominal wall. The obturator is inserted into the working channel of the cannula and pushed through the body wall with a penetration force of sufficient magnitude to result in penetration of the body wall. Alternatively, the cannula with an obturator is passed through an incision formed by the "Hassan," or cut-down, technique, which includes incremental incisions through the body wall until the body wall is incised through its entire thickness. Once the cannula has traversed the body wall, the obturator can be removed.

With the cannula in place in the body wall, various instruments may be inserted through the cannula into the body cavity. One or more cannulas may be used during a procedure. During the procedure, the surgeon manipulates the instruments in the cannulas, sometimes using more than one instrument at a time. The manipulation of an instrument by a surgeon may cause frictional forces between the instrument and the cannula in which the instrument is inserted. These frictional forces may result in movement of the cannula in an inward or outward direction within the body wall. If the cannula is not fixed in place, the proximal or distal motions of the instruments through the cannula may potentially cause the cannula to slip out of the body wall or to protrude further into the body cavity, possibly leading to injury to the patient.

The surfaces of the cannula associated with a trocar are generally smooth. The smoothness of a cannula surface makes placement of the cannula through a body wall relatively easy and safe. However, a smooth cannula may not have the desired retention characteristics once the cannula has been placed through a body wall. This may present problems as instruments and specimens are removed from a body cavity through the cannula and the associated seal systems of the trocar. It is highly desirable for a cannula to remain fixed in the most appropriate position once placed. Additionally, if the Hassan technique is used, the incision may be larger than the cannula that may be placed through the incision. Therefore, it is necessary to provide a means to seal the incision site after the cannula has been inserted in order to insufflate a patient.

Many solutions to the issue of trocar-cannula fixation or stabilization have been formed. These solutions include an inflatable balloon attached to the distal portion of the cannula with a thick foam bolster proximal to the insertion point into the body wall, raised threads or raised rings associated with the outer surface of the cannula, mechanically deployable enlarging portions arranged at the distal end of a cannula and suture loops or hooks associated with the proximal end of the trocar. These solutions have provided some degree of fixation or stabilization, but they have often led to cannulas having a larger outside diameter. Further, the thick foam bolster associated with balloon trocars has reduced the usable length of the cannula. There remains a need for a cannula fixation or stabilization device that includes a sleeve having attachment means that minimize the increase in diameter. Additionally, the cannula fixation or stabilization device may include a lower profile and increase the working length of the cannula.

SUMMARY OF THE INVENTION

The invention is directed to trocars that are used in laparoscopic surgeries and, more specifically, to balloon trocars used generally after the Hassan technique is used to gain entry into a body cavity, such as the abdominal cavity. The balloon on the distal of the trocar provides a sealing means for the incision. Once an incision is made to gain entry to the body cavity, the trocar is inserted through the incision until the balloon is within the body cavity. The balloon is then inflated and a bolster located toward the proximal end of the cannula is moved distally along the length of the cannula in order to compress the balloon against the inside of the body wall and seal the incision. With the bolster against the outer surface of the body wall, the balloon is maintained in compression against the inner surface of the body wall. In this manner, a seal is created between the balloon and the body wall, thereby allowing a surgeon to insufflate a patient. The balloon trocar includes a cannula assembly, a trocar seal and an obturator. The cannula assembly includes a cannula and an outer sleeve.

In one embodiment, the cannula includes a substantially longitudinal tube having a proximal end, a distal end, and a lumen extending between the proximal end and the distal end. A proximal portion of the cannula has a first, larger periphery and a distal portion of the cannula has a second, smaller periphery. The cannula has an annular groove on the outer surface of the distal portion of the cannula toward the distal end of the cannula. The cannula also includes a plurality of channels on the outer surface of the distal portion of the cannula. The channels extend along the length of the cannula from substantially a proximal end of the distal portion of the cannula distally to a point proximal to the annular groove near the distal end of the cannula. The sleeve includes a substantially longitudinal tube having a proximal end, a distal end, and a lumen extending between the proximal end and the distal end. The sleeve also includes a proximal portion having a first, larger periphery, a distal portion having a second, smaller periphery, and an annular groove on the outer surface of the distal portion of the sleeve toward the distal end of the sleeve. The lumen of the sleeve is configured to accept the cannula. The cannula assembly also includes a balloon that includes a tubular sleeve. Additionally, the cannula assembly includes a seal. The sleeve is positioned over the cannula with the proximal portion of the sleeve fitting over at least a distal region of the proximal portion of the cannula and the distal portion of the sleeve fitting over at least a portion of the distal portion of the cannula. The distal end of the sleeve is positioned proximal to a distal end of the plurality of channels on the outer surface of the cannula. The cannula and the sleeve are coupled together at the proximal portion of the cannula and the proximal portion of the sleeve. The seal is positioned between the cannula and the sleeve and compressed sufficiently to form a seal between the cannula and the sleeve. The balloon is sufficiently long to extend between and cover the annular groove on the outer surface of the distal portion of the cannula and the annular groove on the outer surface of the distal portion of the sleeve. The space between the outer surface of the cannula with the channels, the inner surface of the sleeve, the seal and the balloon forms a substantially closed chamber.

In one aspect, the proximal portion of the cannula includes a substantially cylindrical portion having a first, larger circumference and the distal portion of the cannula includes a substantially cylindrical portion having a second, smaller circumference, and the proximal portion of the sleeve includes a substantially cylindrical portion having a first, larger circumference and the distal portion of the sleeve includes a substantially cylindrical portion having a second, smaller circumference. In another aspect, the plurality of channels on the outer surface of the cannula includes a plurality of substantially longitudinal grooves that are substantially parallel to a longitudinal axis of the cannula. In another aspect, the seal is an o-ring, such as an o-ring made of a material having a hardness of about 40 Shore A. In another aspect, the seal is positioned between the proximal portion of the cannula and the proximal portion of the sleeve. In another aspect, the cannula includes a transition region between the proximal portion of the cannula and the distal portion of the cannula, the sleeve includes a transition region between the proximal portion of the sleeve and the distal portion of the sleeve, and the seal is positioned between the transition region of the cannula and the transition region of the sleeve. In another aspect, the cannula and the sleeve are coupled together at a position proximal to the seal. In another aspect, the means for coupling the cannula to the sleeve includes a snap fitting including at least one projection on the outer surface of the cannula and at least one notch on the inner surface of the sleeve. In another aspect, the snap fitting includes two projections positioned substantially circumferentially opposite each other on the outer surface of the cannula and two notches positioned substantially circumferentially opposite each other on the inner surface of the sleeve. In another aspect, the cannula assembly also includes locking means to substantially prevent the cannula and the sleeve from rotating relative each other about a longitudinal axis of the cannula and a longitudinal axis of the sleeve. In another aspect, the locking means includes a projection on the outer surface of the proximal portion of the cannula and a channel on the inner surface of the proximal portion of the sleeve. In another aspect, the channel is substantially longitudinal and substantially parallel to the axis of the sleeve. In another aspect, the cannula assembly also includes a first winding of thread around the balloon in the area that overlaps the annular groove at the distal portion of the cannula and forces the balloon into that annular groove, and a second winding of thread around the balloon in the area that overlaps the annular groove at the distal portion of the sleeve and forces the balloon into that annular groove. In another aspect, the balloon includes a substantially toroid shape upon inflation of the balloon. In another aspect, the tubular sleeve of the balloon includes an elastomeric tubular sleeve. In another aspect, the cannula assembly also includes a second tubular sleeve that is formed of an elastomeric material and positioned over the tubular sleeve of the balloon. In another aspect, the cannula assembly also includes a first winding of thread around the balloon and second tubular sleeve in the area that overlaps the annular groove at the distal portion of the cannula and forces the balloon and second tubular sleeve into that annular groove, and a second winding of thread around the balloon and second tubular sleeve in the area that overlaps the annular groove at the distal portion of the sleeve and forces the balloon and second tubular sleeve into that annular groove. In another aspect, the sleeve includes an inflation port positioned distal to the seal. In another aspect, the cannula assembly also includes a bolster that is slidably adjustable along the length of the sleeve proximal to the balloon. In another aspect, the bolster includes a base, a clamping mechanism including an over-center lock design positioned at a proximal portion of the base, and a pad including a substantially incompressible gel material positioned at a distal portion of the base. In another aspect, the cannula assembly also includes an obturator positioned within the lumen of the cannula. The obturator includes an elongate shaft extending along a substantially longitudinal axis between a proximal end and a distal end, a distal tip that has a prolate spheroid shape, and a handle portion having a larger periphery than the elongate shaft positioned at a proximal portion of the obturator. The shaft and distal tip of the obturator are sized and configured to slide within the lumen of the cannula. In an operative position, the distal tip of the obturator is positioned distal to the distal end of the cannula and the handle portion of the obturator is positioned proximal to the proximal end of the cannula. In another aspect, the cannula assembly also includes a trocar seal positioned at the proximal portion of the cannula. The trocar seal includes a valve that provides an instrument seal in the presence of an instrument and provides a zero-seal in the absence of an instrument. In another aspect, the trocar seal is removable from the cannula assembly.

These and other features and advantages of the invention will become more apparent with a discussion of embodiments of the invention and reference to the associated drawings.

DESCRIPTION

Figure 1:
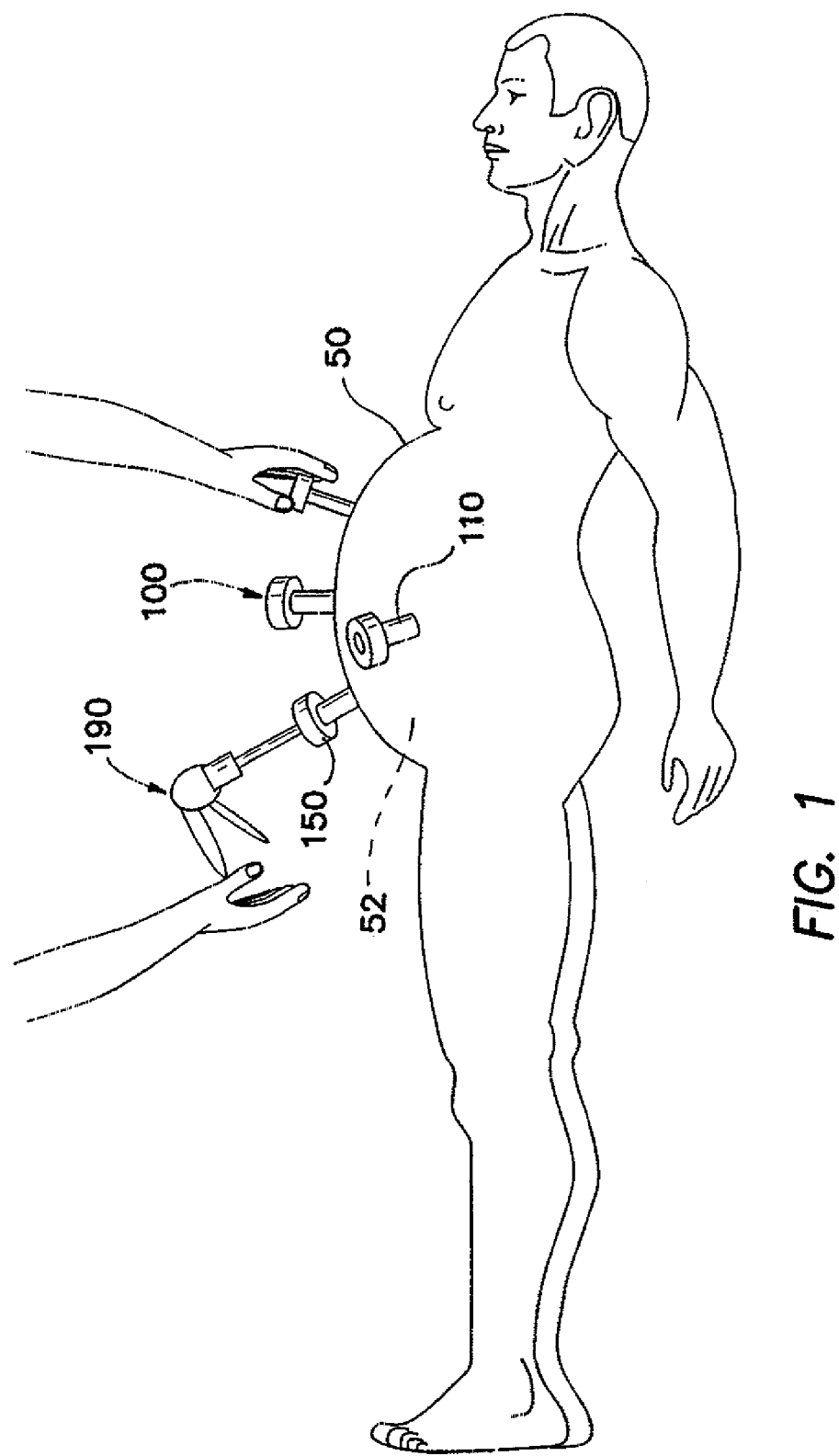
FIG. 1 is a side view of a laparoscopic surgical procedure.
Figure 2:
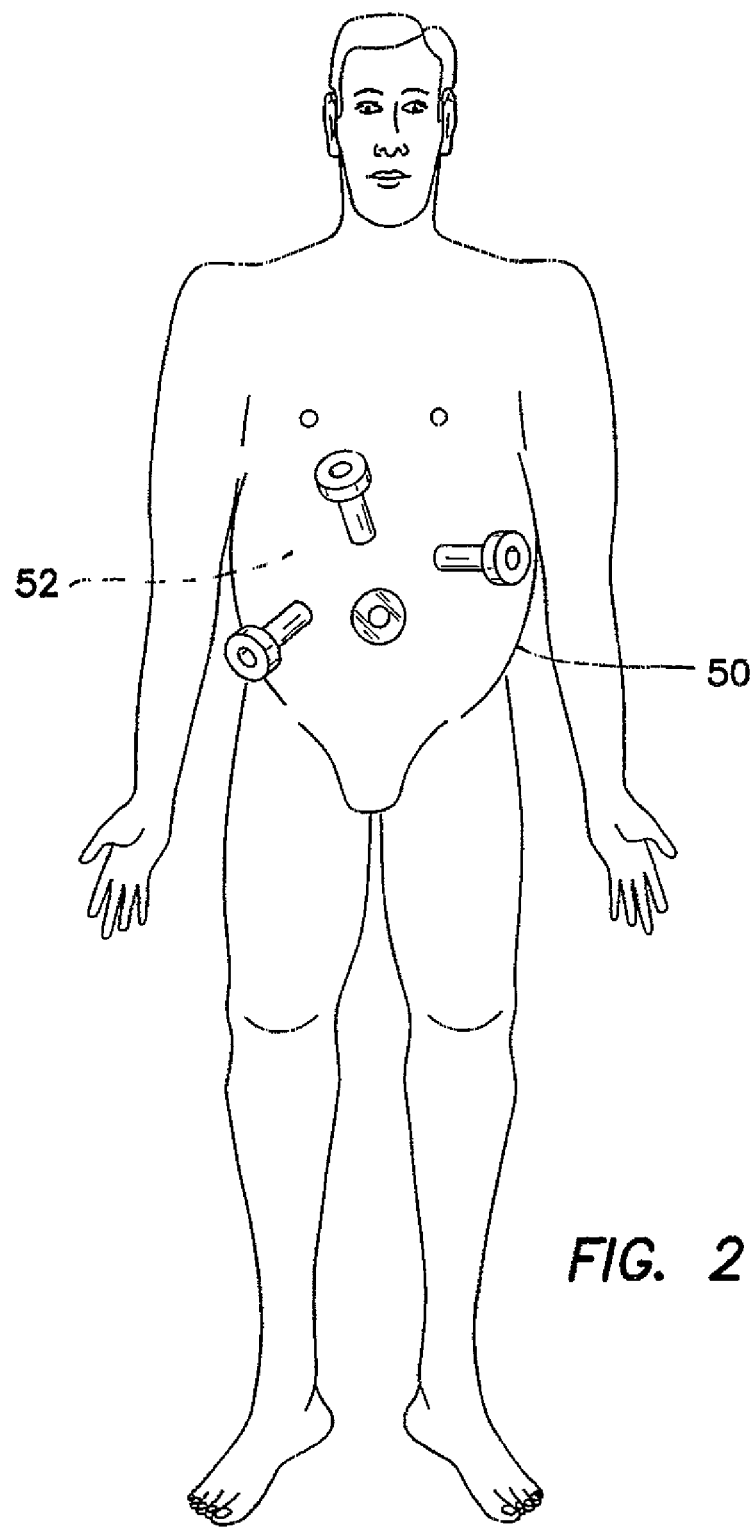
FIG. 2 is a plan view of a laparoscopic surgical procedure showing the placement of trocars.
Figure 5:
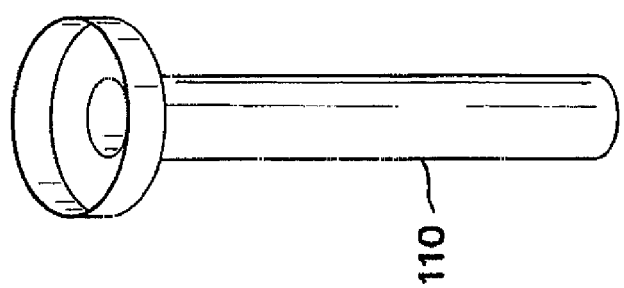
FIG. 5 is a perspective view of a prior art cannula.
Figure 4:
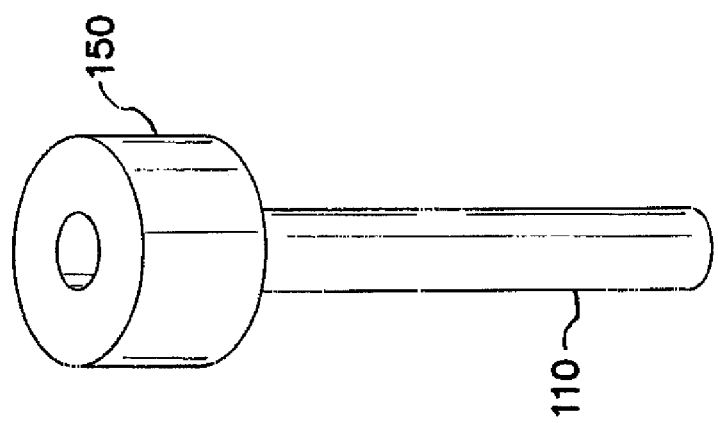
FIG. 4 is a perspective view of a prior art assembled trocar without an obturator.
Figure 3:
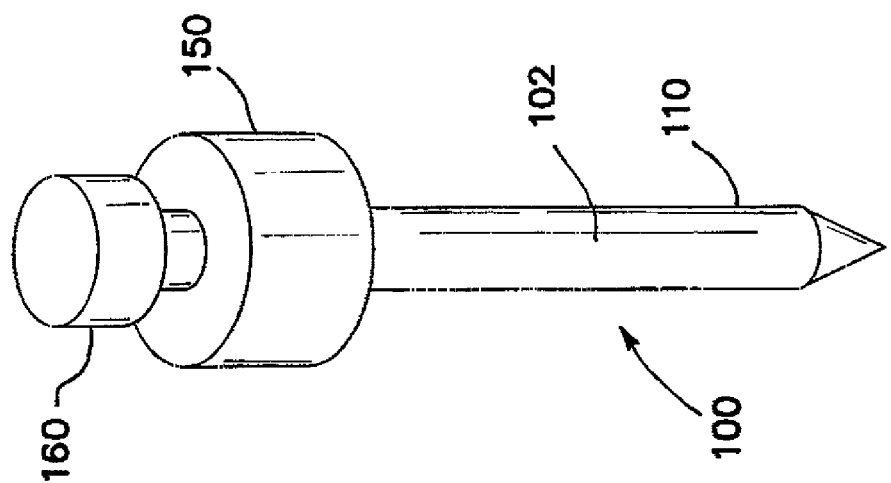
FIG. 3 is a perspective view of a prior art assembled trocar and obturator.

With reference to FIGS. 1 and 2, a typical laparoscopic procedure is illustrated where a plurality of trocars 100 are placed through a body wall 50, such as an abdominal wall, and into a body cavity 52, such as an abdominal cavity. The body cavity 52 is insufflated, or inflated with gas, to distend the body wall 50 and provide a working space for the laparoscopic procedure. The trocars 100 each include a cannula 110 and a seal 150. Positive pressure is maintained within the body cavity 52 by the seal 150 associated with the cannula 110. In addition, the cannula 110 must form a gas-tight seal against adjacent tissue. If positive pressure is lost, either through the seal 150 associated with the cannula 110 or the seal between the cannula and the adjacent tissue, the procedure may be compromised.

As the body cavity 52 is inflated, the body wall 50 may be greatly distended. The access sites may tend to enlarge under the distention of the body wall 50 and compromise the positioning and sealing of the cannula 110. As stated above, the manipulation of instruments 190 used through the trocars 100 may result in movement of the cannulas 110 in either a proximal or distal direction within the access site through the body wall 50. As this occurs, some liquefaction may take place and the preferred relationship between the cannula 110 and the body tissue may be compromised.

Referring now to FIGS. 3-6, a typical assembled trocar 100 is shown having a cannula 110, a seal housing 150 and an obturator 160. The cannula 110 typically has a smooth exterior surface 102 so that it may be inserted through the body wall 50 easily. The seal housing 150 contains a seal system that prevents retrograde gas-flow. The obturator 160 is a cutting or piercing instrument that creates the pathway through the body wall 50 through which the cannula 110 follows. Surgical obturators 160 are generally sized and configured to create a defect in tissue that is appropriate for the associated cannula 110. However, the defect may have a tendency to enlarge during a surgical procedure as the trocar 100 or cannula 110 is manipulated. As an instrument 190 is urged distally and proximally, or inserted and withdrawn, the cannula 110 may move or even be inadvertently withdrawn due to the friction between the instrument 190 and the seal 150 of the trocar housing.

Figure 8:
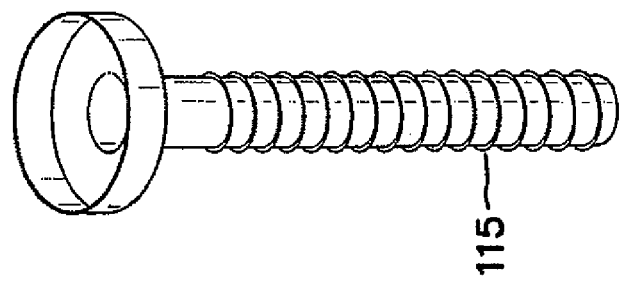
FIG. 8 is a perspective view of a prior art threaded cannula.
Figure 7:
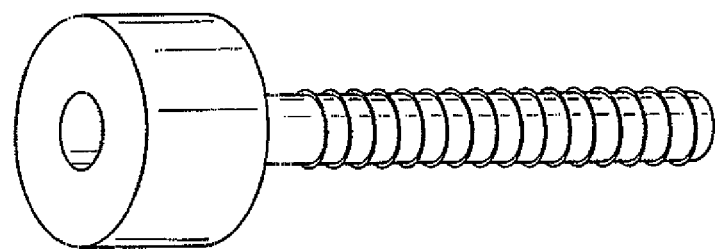
FIG. 7 is a perspective view of a prior art threaded cannula and housing.
Figure 6:
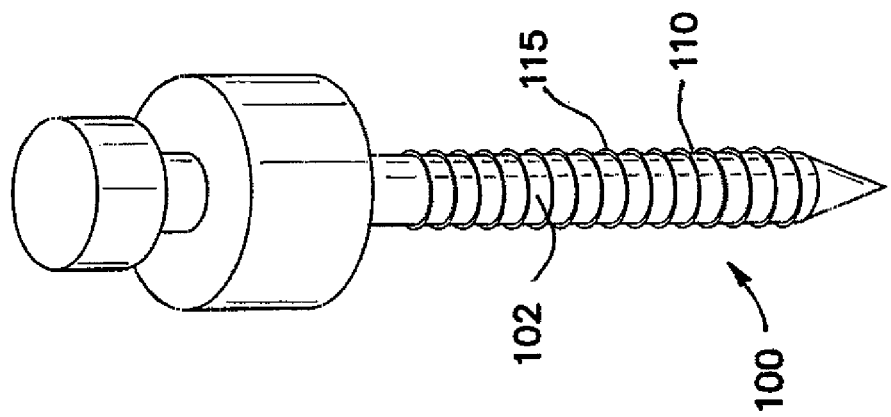
FIG. 6 is a perspective view of a prior art assembled threaded trocar and obturator.
Figures 9, 10:
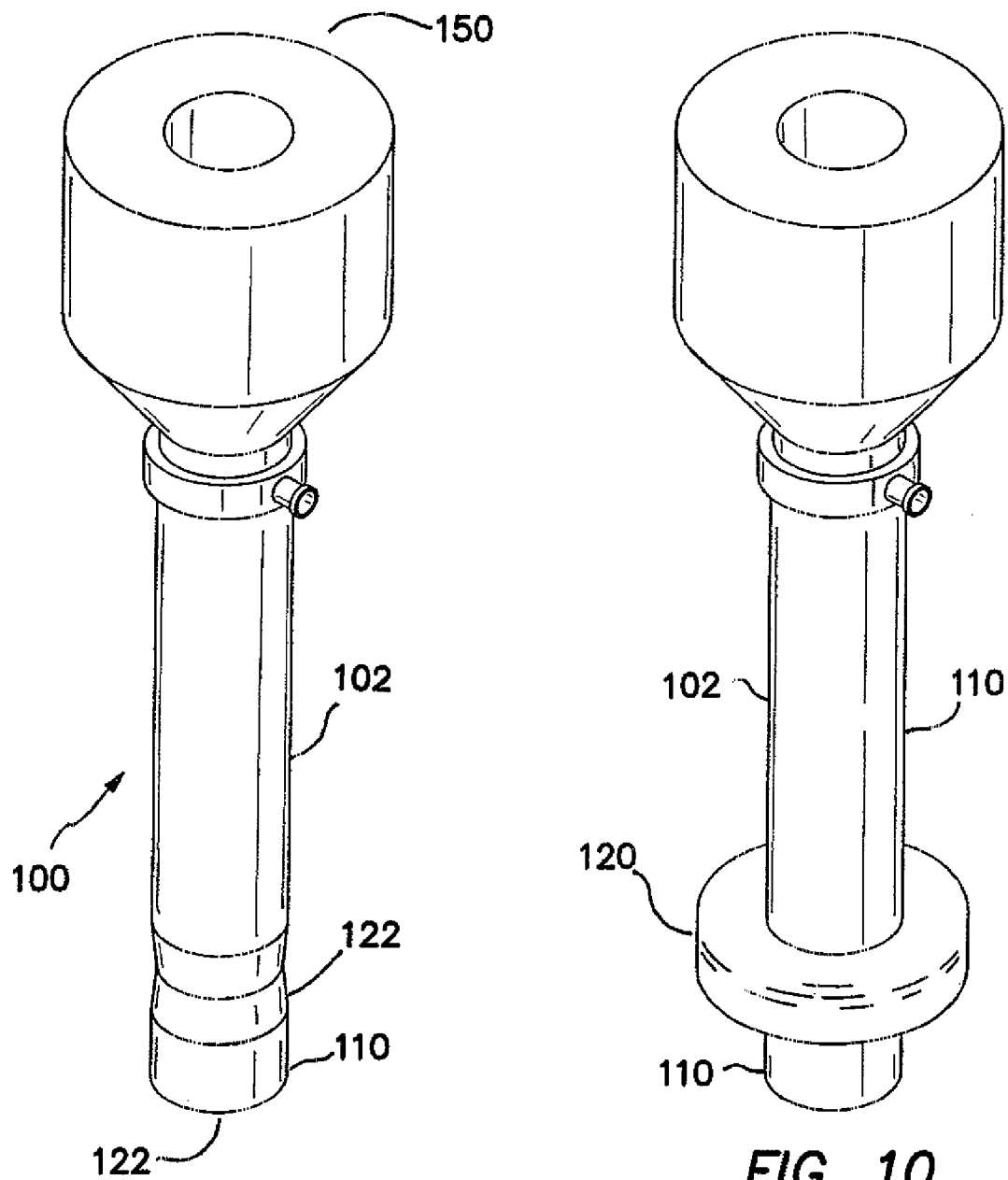
FIG. 9 is a perspective view of a prior art cannula having an uninflated balloon at the distal end.
FIG. 10 is a perspective view of a prior art cannula having an inflated balloon at the distal end.
Figure 11:
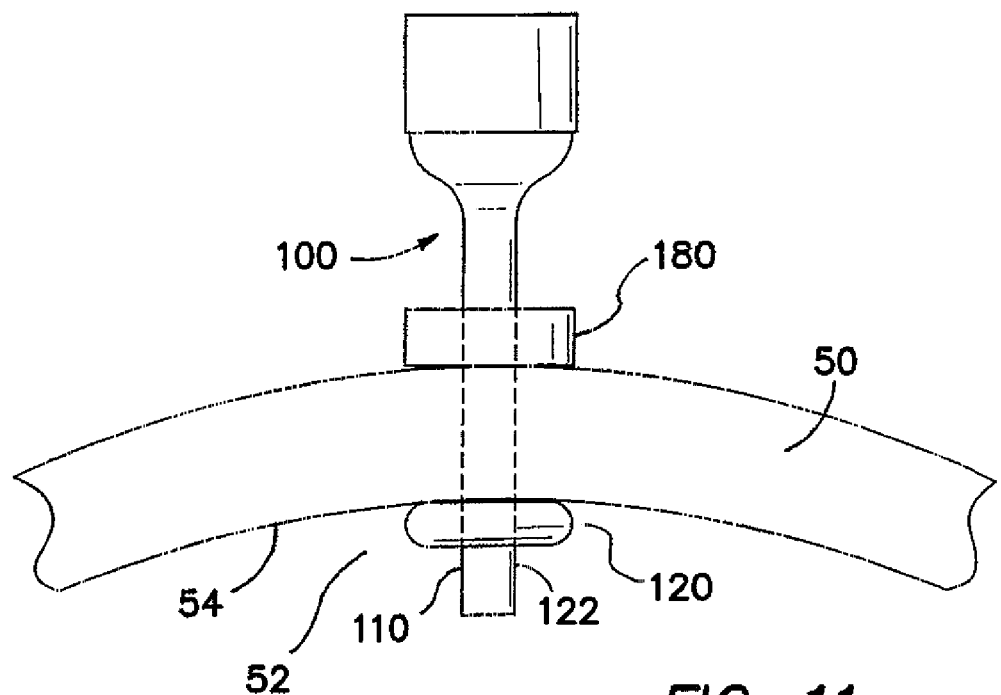
FIG. 11 illustrates a prior art trocar-cannula having a distal retention balloon placed through a body wall in a first position.
Figure 12:
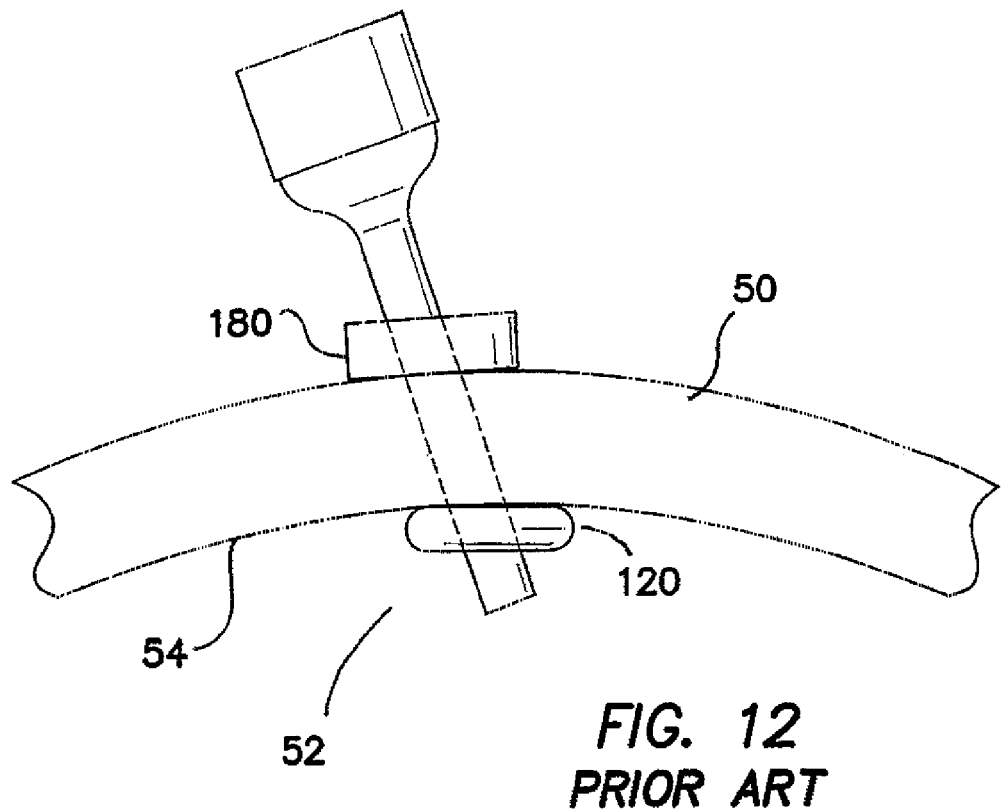
FIG. 12 illustrates a prior art trocar-cannula having a distal retention balloon placed through a body wall in a second position.

With specific reference to FIGS. 6-8, a trocar 100 or access device is shown where the outer surface 102 of the cannula 110 includes a plurality of raised features 115. These raised features 115 are sized and configured to increase resistance to proximal and distal motion as instruments 190 are maneuvered, and especially as specimens are removed, through the trocar 100. The prior art includes either sequential raised rings or a raised coarse-thread 115. While the rings or threads 115 of the prior art may stabilize the cannula 110 to some degree, they do not necessarily seal the cannula 110 against the adjacent tissue of a body wall 50. There may be gas loss associated with the use of these systems. The raised rings or threads 115 also increase the insertion force required to penetrate a body wall 50. The insertion force may be reduced in the instance of a continuous coarse thread 115 in comparison to a sequence of discrete raised rings or features as a threaded cannula 110 may actually be "screwed" into the tissue defect in accordance with the thread direction and pitch, rather than pushed through without appropriate rotation.

With reference to FIGS. 9-12, a surgical access device 100 according to prior art includes a cannula 110 having an inflatable balloon 120 associated with the distal-end portion 122 of the cannula. The balloon 120 is sized and configured to fit snugly around the cannula 110 in the uninflated condition. The balloon 120 is inflated after the cannula 110 is properly placed through the body wall 50 and into the body cavity 52. The balloon 120 is generally held against the interior surface 54 of the body wall 50 by a counter-force that is associated with a sliding counter-force member, such as a foam bolster 180. The bolster 180 is associated with the proximal portion of the cannula 110. The balloons 120 associated with the devices of the prior art are typically "thick-walled" structures constructed as part of the cannula 110. The balloon 120 is generally bonded to the distal-end portion 122 of the cannula 110 and an inflation channel or lumen is provided within the wall of the cannula 110.

Figure 13:
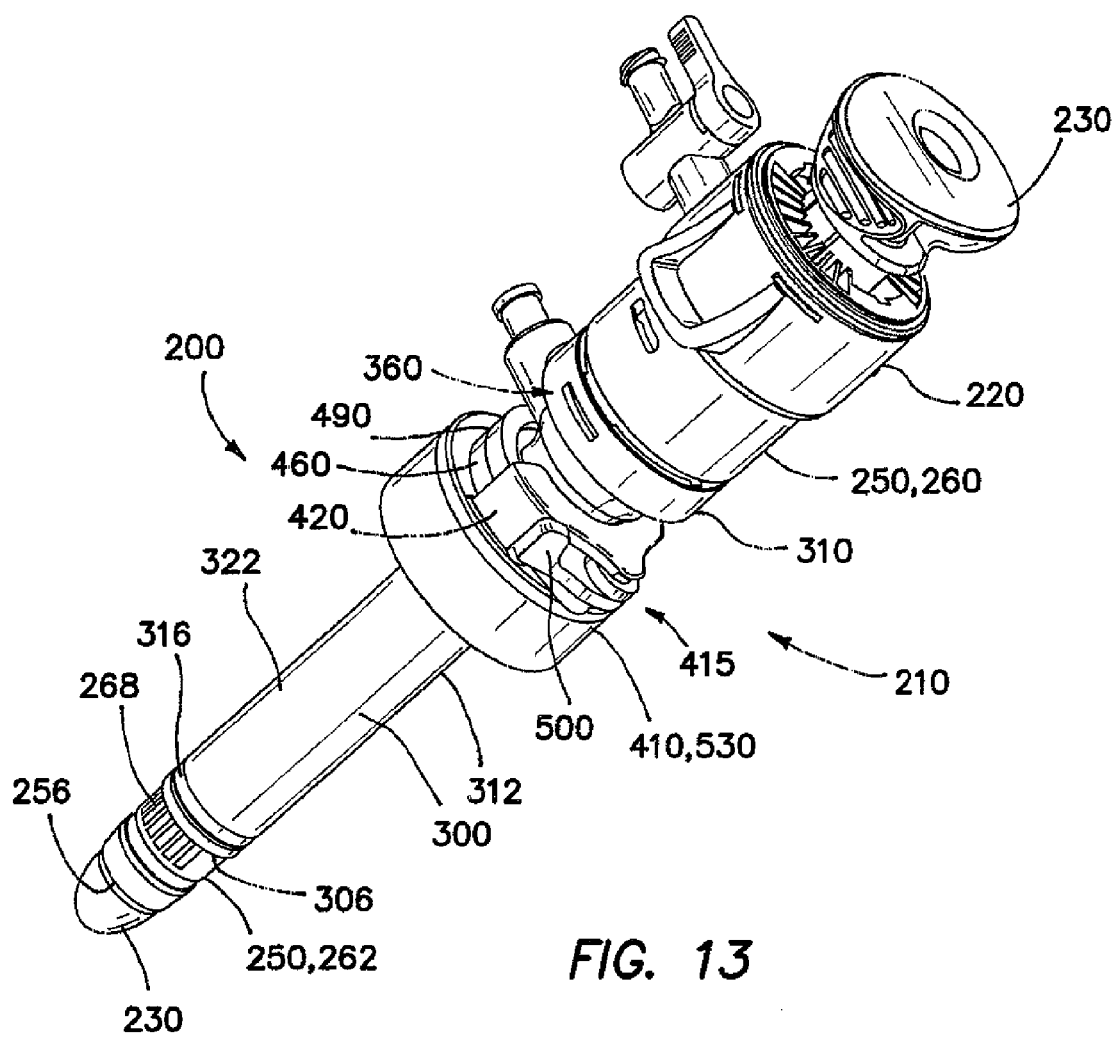
FIG. 13 is a perspective view of a balloon trocar having a bolster.

Referring to FIG. 13, one embodiment of the balloon trocar 200 includes a cannula assembly 210, a trocar seal 220 and an obturator 230. The cannula assembly 210 includes a cannula 250 and an outer sleeve 300.

Figure 14:
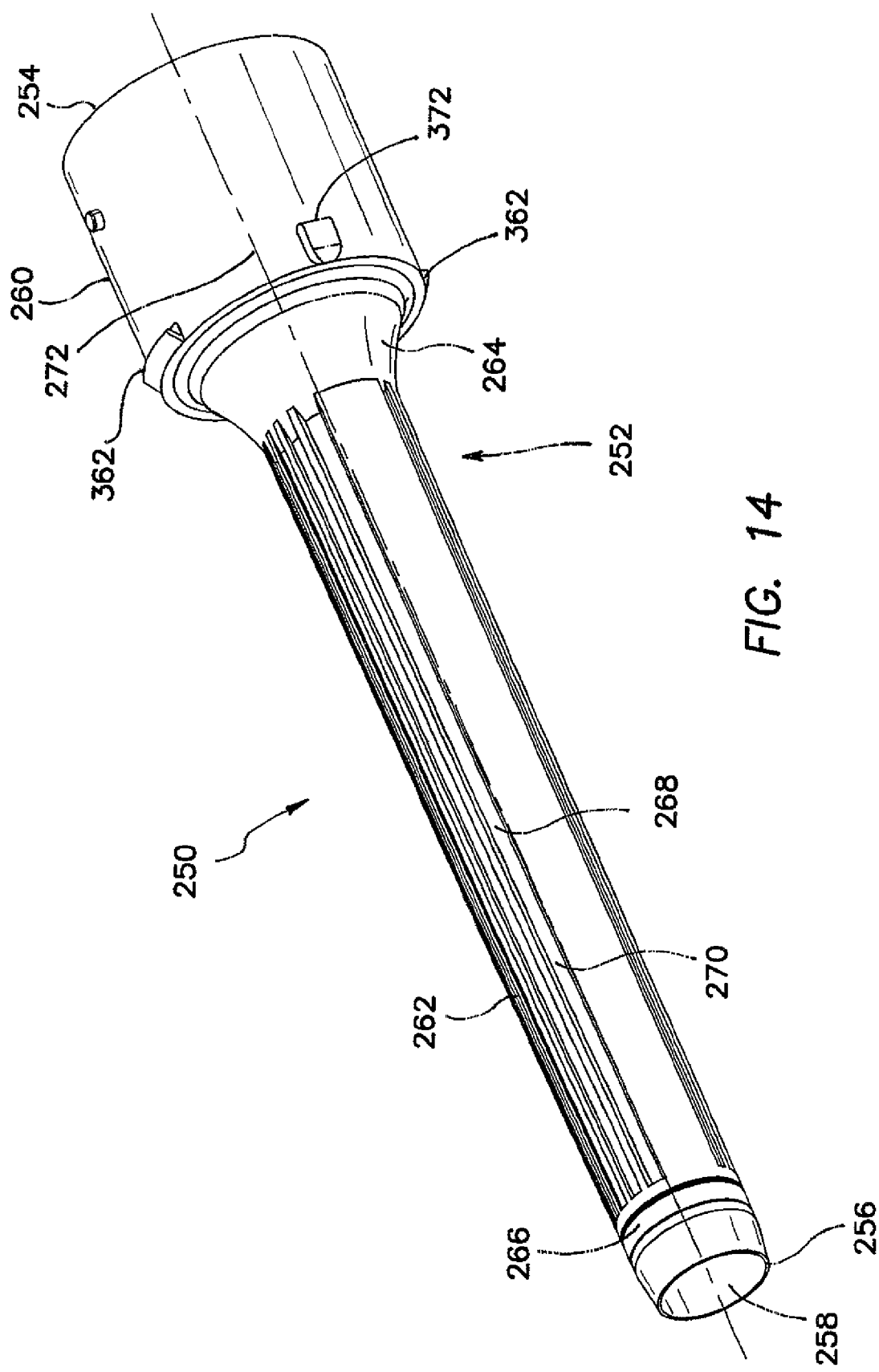
FIG. 14 is a perspective view of a cannula portion of the balloon trocar of FIG. 13.

Referring to FIG. 14, the cannula 250 includes a substantially longitudinal tube 252 having a proximal end 254, a distal end 256, and a lumen 258 therebetween. The cannula 250 may include at least a proximal portion 260 having a first, larger periphery and a distal portion 262 having a second, smaller periphery. In one embodiment, the proximal portion 260 and distal portion 262 of the cannula 250 may each include a substantially cylindrical portion, with the proximal portion 260 having a first, larger circumference and the distal portion 262 having a second, smaller circumference. The cannula 250 may also include a transition region 264 between the proximal portion 260 and the distal portion 262. The lumen 258 of the cannula 250 may be substantially smooth and configured to accept the obturator 230 (see FIG. 13). The proximal portion 260 of the cannula 250 may be configured to accept the trocar seal 220 (see FIG. 13). The outer surface of the distal portion 262 of the cannula 250 includes an annular groove 266 toward the distal end 256 of the distal portion of the cannula. The annular groove 266 may lie within a plane that is substantially perpendicular to a longitudinal axis 272 of the cannula 250. Additionally, the outer surface of the distal portion 262 of the cannula 250 includes a plurality of channels 268 extending along the length of the cannula from substantially the proximal end of the distal portion of the cannula distally to a point proximal to the annular groove 266 near the distal end 256 of the distal portion of the cannula. The plurality of channels 268 is adapted to facilitate the flow of gasses or fluids therethrough. In one embodiment, the plurality of channels 268 may include a plurality of substantially longitudinal grooves 270 that are substantially parallel to the longitudinal axis 272 of the cannula 250. In one embodiment, the cannula 250 may be made of a polymeric material, such as a polycarbonate material.

Figure 15:
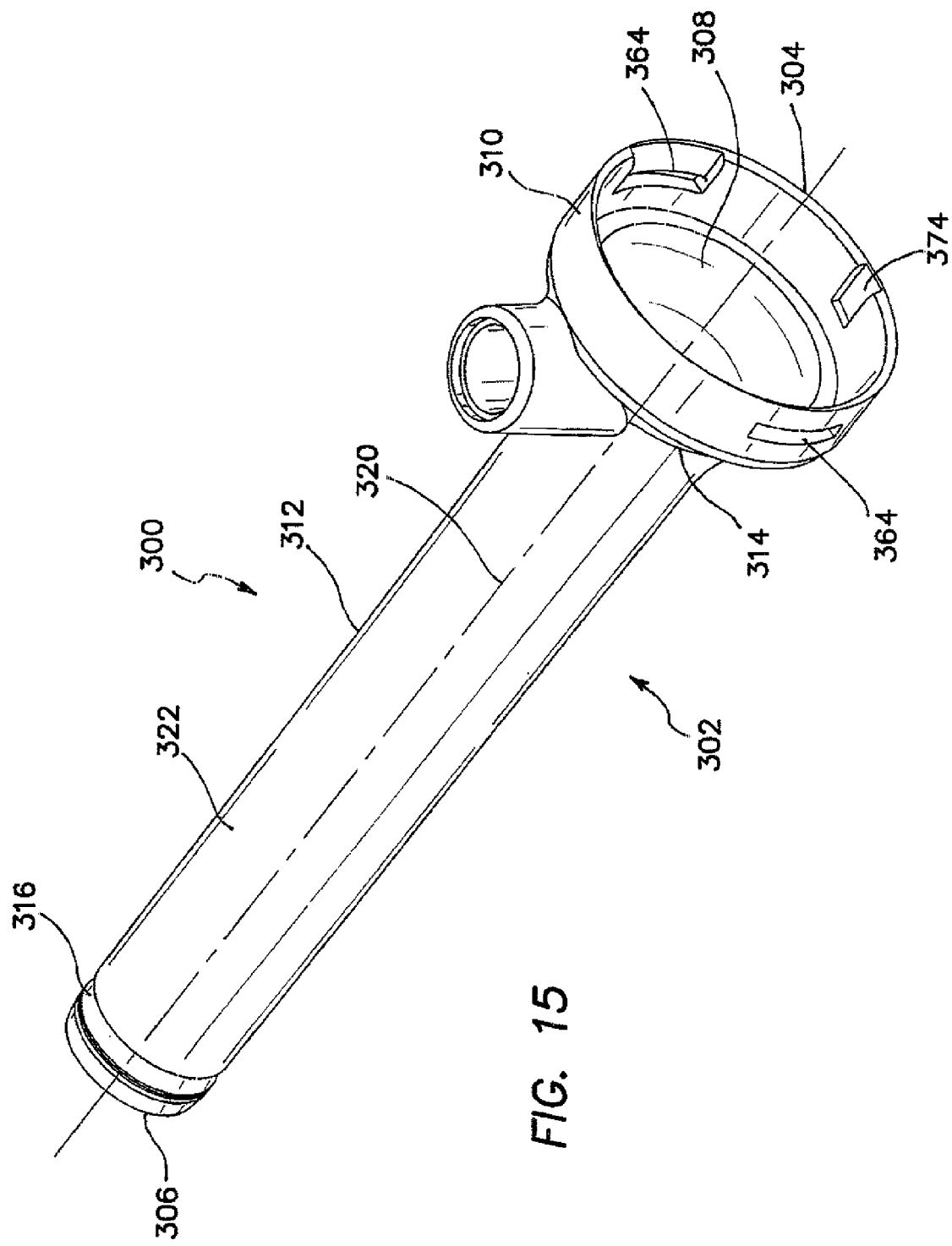
FIG. 15 is a perspective view of a sleeve portion of the balloon trocar of FIG. 13.

Referring to FIG. 15, the outer sleeve 300 of the cannula assembly 210 includes a substantially longitudinal tube 302 having a proximal end 304, a distal end 306, and a lumen 308 therebetween. The sleeve 300 may also include at least a proximal portion 310 having a first, larger periphery and a distal portion 312 having a second, smaller periphery. In one embodiment, the proximal portion 310 and distal portion 312 of the sleeve 300 may each include a substantially cylindrical portion, with the proximal portion 310 having a first, larger circumference and the distal portion 312 having a second, smaller circumference. The sleeve 300 may include a transition region 314 between the proximal portion 310 and the distal portion 312. The lumen 308 of the sleeve 300 is configured to accept the cannula 250 (see FIG. 13) and may be substantially smooth. An outer surface 322 of the distal portion 312 of the sleeve 300 includes an annular groove 316 toward the distal end 306 of the distal portion of the sleeve. The annular groove 316 may lie within a plane that is substantially perpendicular to a longitudinal axis 320 of the sleeve 300. In one embodiment, the sleeve 300 may be made of a polymeric material, such as a polycarbonate.

Referring again to FIG. 13, with the sleeve 300 positioned over the cannula 250, the proximal portion 310 of the sleeve 300 fits over at least a distal region of the proximal portion 260 of the cannula and the distal portion 312 of the sleeve fits over at least a portion of the distal portion 262 of the cannula. Additionally, with the sleeve 300 positioned over the cannula 250, the distal end 306 of the sleeve 300 is positioned proximal to a distal end of the plurality of channels 268 on the outer surface of the cannula 250.

Figure 16:
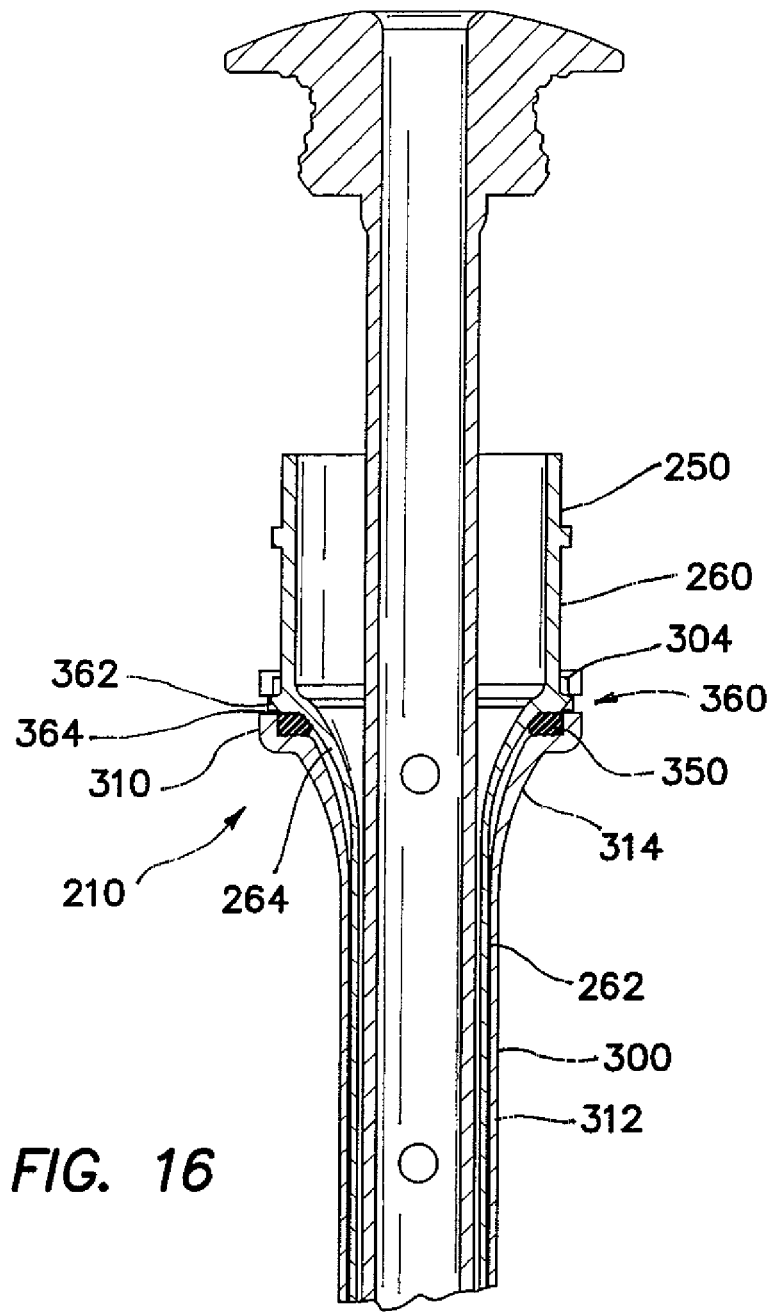
FIG. 16 is a partial plan view in cross section depicting the cannula portion, the sleeve portion, a seal, and an obturator of the balloon trocar of FIG. 13.

As stated above, the cannula assembly 210 includes the cannula 250 and the sleeve 300. Referring now to FIG. 16, to substantially prevent gas or fluid from leaking between the proximal end 304 of the sleeve 300 and the proximal portion 260 of the cannula 250, a seal, such as an o-ring 350, may be positioned between the cannula and the sleeve. In one embodiment the seal, such as the o-ring 350, is positioned between the outer surface of the cannula 250 and the inner surface of the sleeve 300. In another embodiment, the outer surface of the distal region of the proximal portion 260 of the cannula 250 may include a substantially flat surface, such as a planar surface or a chamfered surface, which communicates between the proximal portion 260 of the cannula and either the transition region 264 or the distal portion 262 of the cannula. Similarly, the inner surface of the distal region of the proximal portion 310 of the sleeve 300 may include a substantially flat surface, such as a planar surface or a chamfered surface, which communicates between the proximal portion 310 of the sleeve and either the transition region 314 or the distal portion 312 of the sleeve. In this embodiment, the seal, such as the o-ring 350, is positioned between the flat surface on the outer surface of the distal region of the proximal portion 260 of the cannula 250 and the flat surface on the inner surface of the distal region of the proximal portion 310 of the sleeve 300.

Referring to FIGS. 13-17, the cannula 250 and the sleeve 300 are coupled together at the proximal portion 260 of the cannula and the proximal portion 310 of the sleeve at a position proximal to the seal, such as the o-ring 350. In one embodiment, the means for coupling the proximal portion 260 of the cannula 250 and the proximal portion 310 of the sleeve 300 includes a snap fitting 360 having at least one projection 362 on the outer surface of the cannula and at least one notch 364 on the inner surface of the sleeve. Alternatively, the projection may be on the inner surface of the sleeve and the notch may be on the outer surface of the cannula. The at least one projection 362 and the at least one notch 364 are positioned such that when the projection is positioned within the notch, the seal, such as the o-ring 350, is compressed sufficiently to form a seal between the cannula 250 and the sleeve 300. In one embodiment, the seal, such as the o-ring 350, is made from a soft, compressible material. In one aspect, the o-ring 350 is made of a silicone having a hardness of about 40 Shore A. In one embodiment, the snap fitting 360 includes two projections 362 positioned substantially circumferentially opposite each other on the outer surface of the cannula and two notches 364 positioned substantially circumferentially opposite each other on the inner surface of the sleeve 300. Other means for coupling the sleeve 300 to the cannula 250 that are well known in the art may also be used, such as other mechanical means or adhesive bonding.

Figure 18:
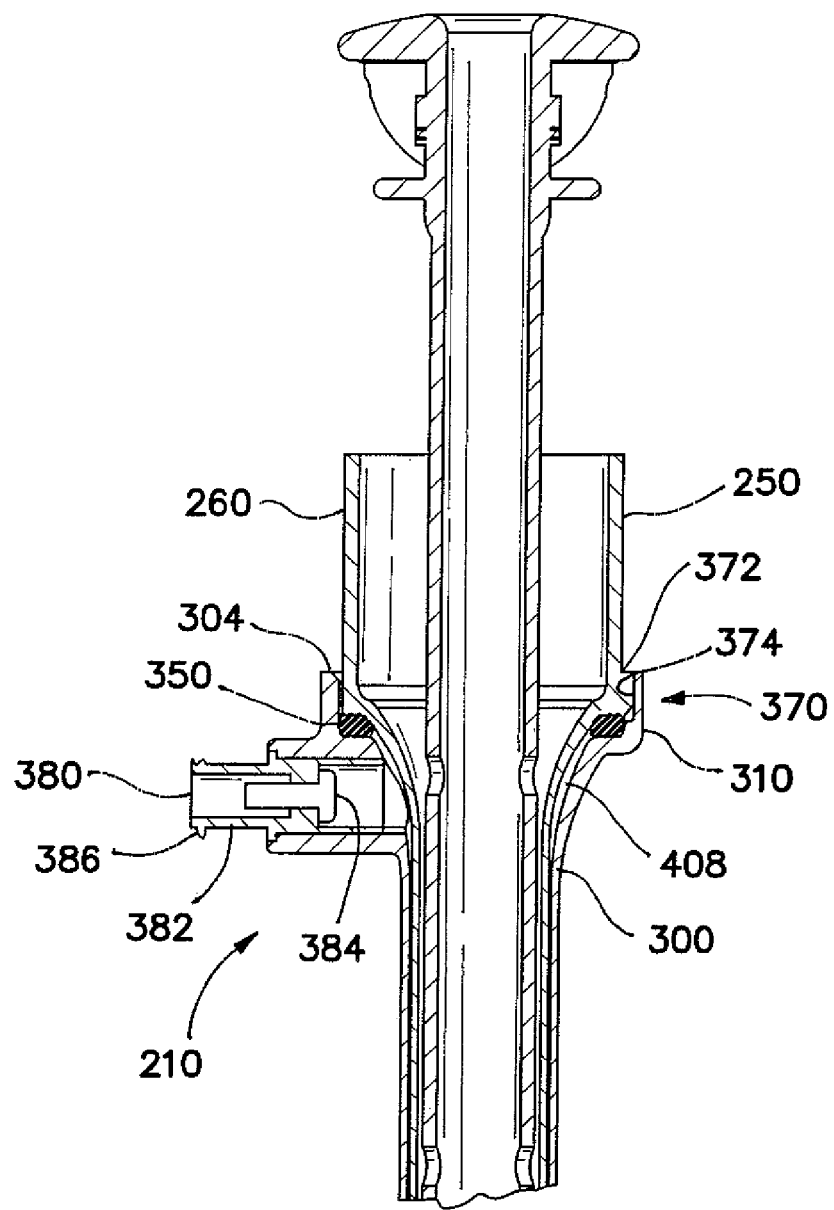
FIG. 18 is a partial plan view in cross section similar to FIG. 16 and including a port portion of the sleeve portion of the balloon trocar.

Referring to FIGS. 14, 15 and 18, the cannula assembly 210 also includes a locking means 370 to substantially prevent, or minimize, the cannula 250 and the sleeve 300 from rotating relative each other about the longitudinal axes 272, 320 while the cannula and sleeve are coupled together. In one embodiment, the locking means 370 includes a projection 372 on the outer surface of the cannula 250 and a channel 374 on the inner surface of the sleeve 300. In one embodiment, the projection 372 is positioned on the outer surface of the proximal portion 260 of the cannula 250 and the channel 374 is positioned on the inner surface of the proximal portion 310 of the sleeve 300 and extends to the proximal end 304 of the sleeve. Alternatively, the projection 372 may be positioned on the inner surface of the proximal portion 310 of the sleeve 300 and the channel 374 may be positioned on the outer surface of the proximal portion 260 of the cannula 250. If the channel 374 is positioned on the sleeve 300, the channel may either be through the entire thickness of the wall of the sleeve or through only a portion of the thickness of the wall of the sleeve. To substantially prevent or minimize rotation between the cannula 250 and the sleeve 300, the channel 374 is substantially longitudinal and substantially parallel to the axis 320 of the sleeve 300. The projection 372 may include any shape that fits within the walls of the channel 374 and facilitates the prevention or minimization of rotation between the cannula 250 and the sleeve 300. In one embodiment, the projection 372 is substantially cylindrical while in another embodiment the projection is substantially rectangular.

Figure 19:
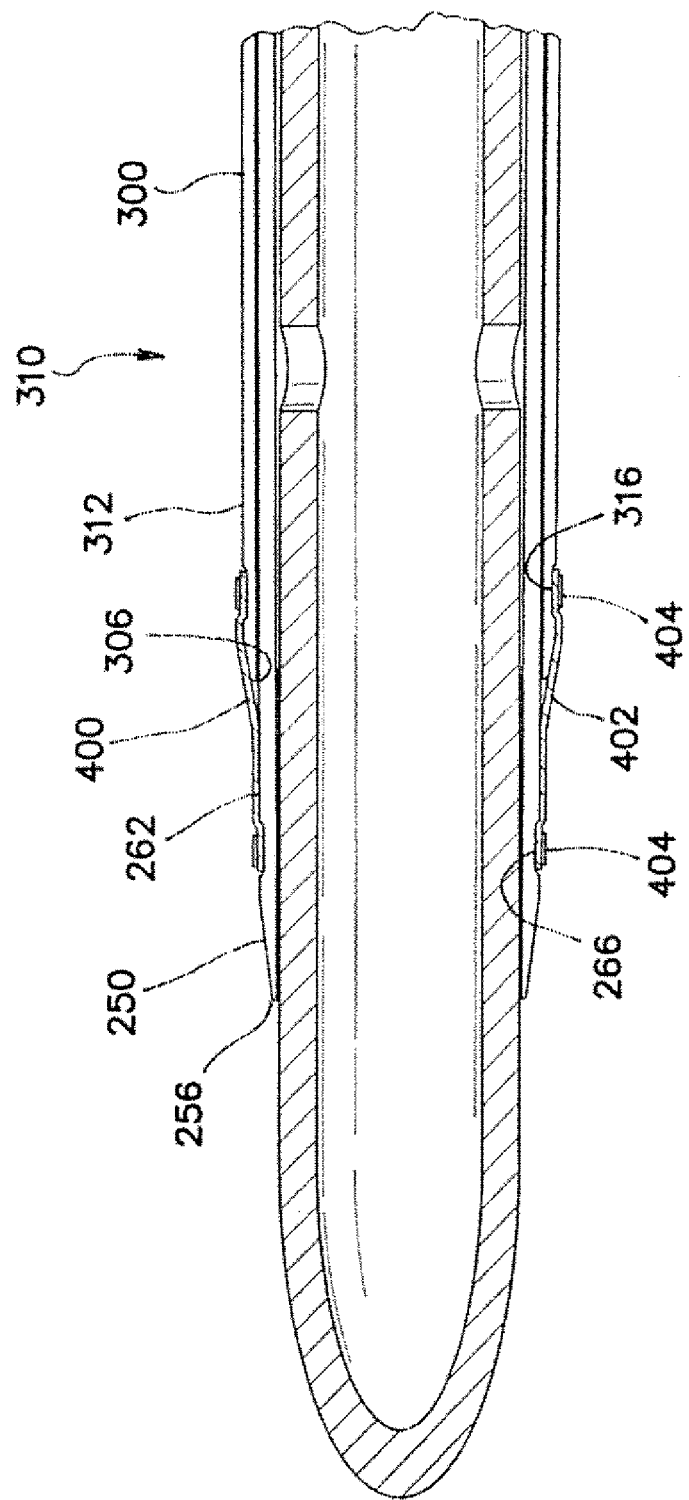
FIG. 19 is a partial plan view in cross section depicting a distal portion of the cannula portion, sleeve portion, obturator and a balloon coupled between the cannula portion and sleeve portion by windings of thread.

Referring to FIG. 19, the cannula assembly 310 also includes a balloon 400. In one embodiment, the balloon includes a tubular sleeve 402. The tubular sleeve 402 may include an elastomeric material. Elastomeric materials that may be used to make the balloon 400 include silicone, polyisoprene, and urethane. In other embodiments, the balloon 400 may be made of other materials, such as MYLAR, that may be folded onto the cannula 250 and sleeve 300 and inflated into a larger profile. The balloon 400 may be cut to length prior to installation onto the cannula 250 and sleeve

300 such that the balloon is sufficiently long to extend between and cover the annular grooves 266, 316 at the distal portions 262, 312 of the cannula and sleeve. The balloon 400 is slid over the distal end 256 of the cannula 250 and the distal end 306 of the sleeve 300 until it covers the annular grooves 266, 316 in the cannula and sleeve.

In one embodiment, the balloon 400 is fixed in place by winding thread 404 around the balloon in the areas that overlap of the annular grooves 266, 316 at the distal portions 262, 312 of the cannula 250 and sleeve 300. Winding the balloon 400 with thread 404 forces the portion of the balloon that overlaps the annular grooves 266, 316 into the annular grooves and holds the balloon in place, thereby substantially preventing longitudinal, axial movement of the balloon along the cannula assembly. The grooves 266, 316 are of sufficient depth that forcing the balloon 400 into the annular grooves 266, 316 makes the balloon and winding 404 substantially flush to the cannula 250 and sleeve 300 at the windings, thereby making the cannula assembly 210 substantially smooth. Furthermore, forcing the balloon 400 into the annular grooves 266, 316 with the windings 404 also forms a seal between the balloon and the cannula 250 and between the balloon and the sleeve 300.

Figure 20:
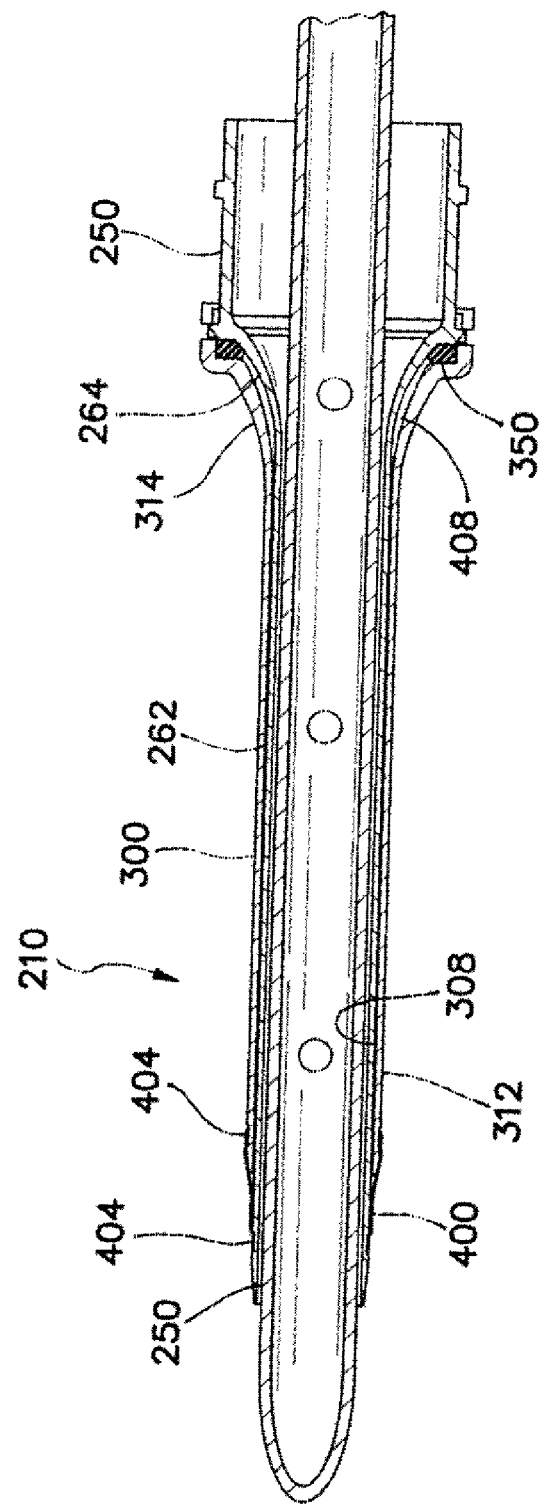
FIG. 20 is a plan view in cross section depicting the balloon trocar.

Referring to FIG. 20, the space between the outer surface of the cannula 250 with the channels 268 (see FIG. 14), the inner surface of the sleeve 300, the o-ring 350, and the balloon 400 with the windings 404 form a substantially closed chamber 408. In one embodiment, the channels 268 on the outer surface of the cannula 250 are formed into the wall of the cannula so as not to increase the overall thickness of the wall of a standard cannula. The lumen 308 of the sleeve 300 may be configured to provide minimal space between the distal portion 312 of the sleeve and the distal portion 262 of the cannula 250, thereby minimizing the overall profile of the cannula assembly 210. The gap between the transition regions 264, 314 of the cannula 250 and the sleeve 300 may be larger than the gap between the distal portions 262, 312 in order to more evenly distribute gas or fluid through the channels 268 on the outer surface of the cannula 250 during inflation and deflation of the balloon.

The balloon 400 may be made to take on one of many different shapes upon inflation of the balloon. In one embodiment, the balloon 400 may include a substantially toroid shape upon inflation. In another embodiment, the balloon may include a disc shape upon inflation. In another embodiment, the balloon 400 may be a fluted balloon. In one embodiment, different shapes for the balloon 400 may be attained by varying the thickness about the tubular sleeve 402 that forms the balloon or by pre-molding a different shape for the balloon.

Figure 21:
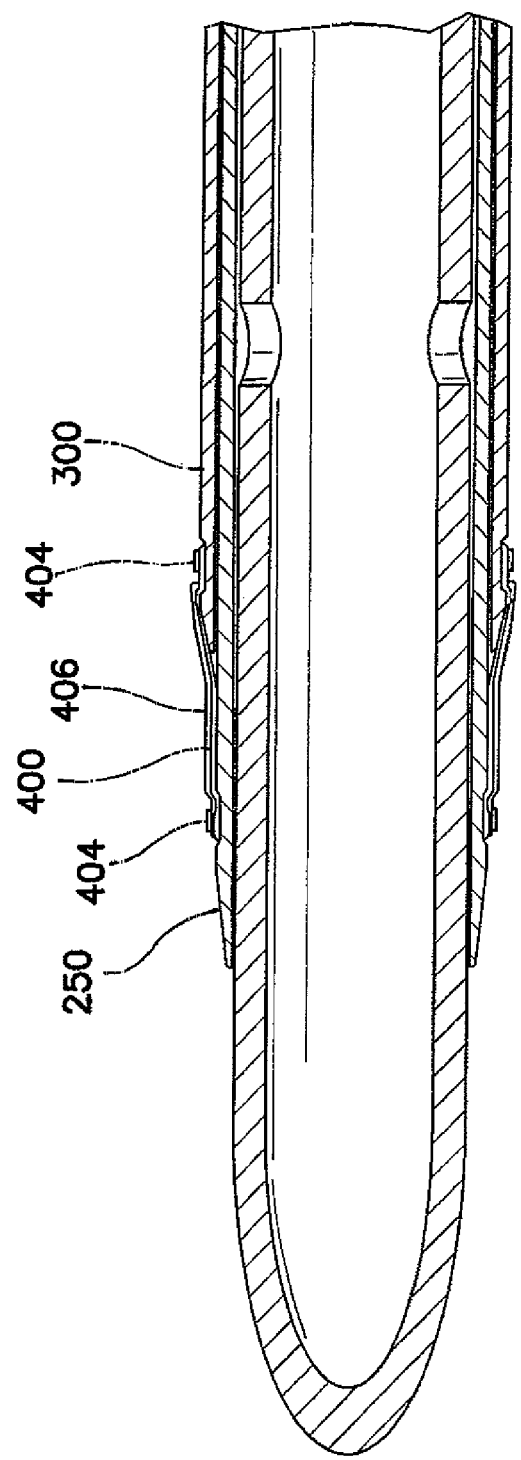
FIG. 21 is a partial plan view in cross section depicting a distal portion of the cannula portion, sleeve portion, obturator and the balloon coupled between the cannula portion and sleeve portion with a balloon having a second layer.

The balloon 400 should have sufficient impermeability properties to substantially prevent inflation gas or fluid from permeating through a wall of the balloon. Additionally, the balloon should bias toward a deflated state during deflation of the balloon. Referring to FIG. 21, when using a balloon material that does not possess adequate properties to bias the balloon toward deflation, an outer layer 406 may be positioned and fixed over the balloon. The outer layer 406 may include silicone, latex, polyisoprene, rubber, or other biocompatible elastomeric materials that are well known in the art. The outer layer 406 may be wound onto the cannula 250 and sleeve 300 together with the balloon 400, as described above.

Referring again to FIG. 18, the sleeve 300 includes an inflation port 380 positioned to be distal to the seal, such as the o-ring 350. The inflation port 380 provides a pathway for gas or fluid to be introduced and removed from the chamber 408. In one aspect, the inflation port 380 may include a normally closed check valve 382 having a spring-loaded plunger 384. In a further aspect, the check valve 380 may include a Luer lock 386. It is contemplated that other inflation ports that are well known in the art may be used.

Referring again to FIG. 13, the trocar seal 220 may include a valve that provides an instrument seal in the presence of an instrument, such as the obturator 230, and a zero-seal in the absence of an instrument. The trocar seal 220 may also be removable from the cannula assembly 210. Removal of the trocar seal 220 is useful for tissue removal through the cannula assembly 210 and for rapid release of insufflation gasses.

Figure 22:
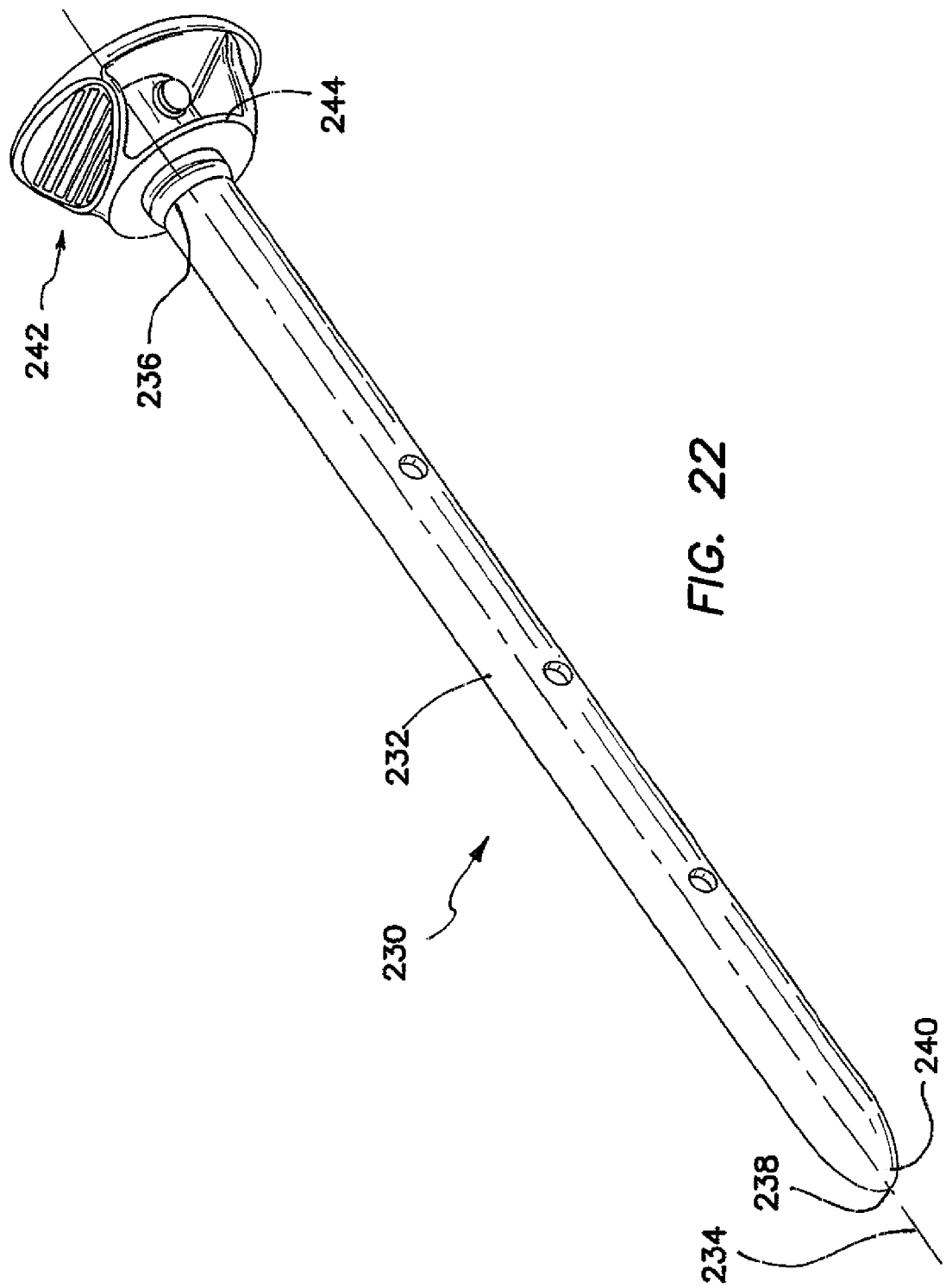
FIG. 22 is a perspective view of the obturator.

Referring to FIG. 22, the obturator 230 includes an elongate shaft 232 extending along a substantially longitudinal axis 234 between a proximal end 236 and a distal end 238. A distal tip 240 of the elongate shaft 232 may include a prolate spheroid shape. The elongate shaft 232, including the distal tip 240, is sized and configured to slide within the lumen 258 of the cannula 250 (see FIGS. 16 and 19). A proximal portion 242 of the obturator 230 may include a handle portion 244 having a larger periphery than the elongate shaft 232 to facilitate advancing and retracting the obturator within the lumen 258 of the cannula 250. In an operative position, the distal tip 240 of the obturator 230 is positioned distal to the distal end 256 of the cannula 250 and the handle portion 244 of the obturator is positioned proximal to the proximal end 254 of the cannula.

The obturator 230 may be made of a polymeric material, such as a polycarbonate. Those familiar with the art will recognize that the obturator 230 may be made of other materials that are well known in the art and are considered within the scope of the present invention. In comparison to obturators having distal tips with a spheroid shape, the distal tip 240 of the obturator 230 having a prolate spheroid shape requires a lower insertion force to insert the trocar into a body through an incision within a body wall. The prolate spheroid shape of the distal tip 240 of the obturator 230 also reduces the likelihood of injuring tissue or organs within the body cavity, in comparison to obturators having distal tips with a more pointed shape. Using the obturator 230 having a distal tip 240 with a prolate spheroid shape, the surgeon can merely nick the peritoneum and dilate or stretch the incision open with the distal tip of the obturator.

Referring again to FIG. 13, a bolster 410 may be used in conjunction with the balloon trocar 200 to assist the balloon to seal around an incision in the body wall 50 through which the balloon trocar is to be inserted with the balloon sealing the incision from within the body cavity 52. The bolster 410 is configured to perform as a cannula fixation device on the outside of the body while the balloon 400 acts as a cannula fixation device on the inside of the body. The bolster 410 is slidably adjustable along the length of the cannula assembly 210 proximal to the balloon 400 and includes a clamping device for locking the bolster in position along the length of the cannula assembly. The balloon 400, on the other hand, is fixed at a location along the length of the cannula assembly 210 and seals against the inner surface of the abdominal wall.

To facilitate the clamping features of the bolster 410, the bolster includes a base 420 and a clamping mechanism 415. The clamping mechanism 415 includes an adjustable collar 460 and a lever 500. The bolster also includes a pad 530 including a substantially incompressible gel material. The clamping features utilize an over-center lock design to maintain the bolster 410 in a fixed position along the length of the cannula assembly 210.

Figure 23:
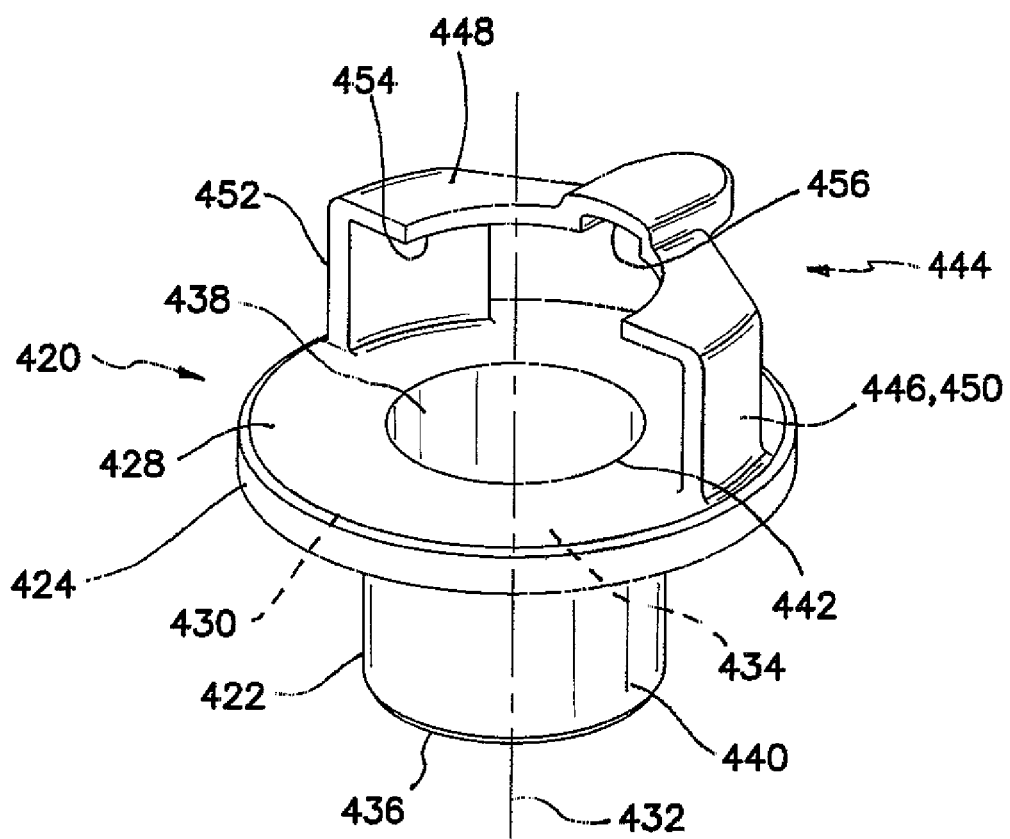
FIG. 23 is a perspective view of a base portion of the bolster of FIG. 13.

Referring to FIG. 23, the base 420 includes a sleeve 422 projecting distally from a flange 424. The flange 424 includes a proximal surface 428 and a distal surface 430. The proximal surface 428 and the distal surface 430 of the flange 424 are substantially parallel to each other and substantially perpendicular to an axis 432 of the base 420. Although the flange 424 is shown as being flat, other shapes, such as rounded shapes, may be used and are contemplated as within the scope of the invention. The sleeve 422 portion of the base 420 includes a proximal end 434, a distal end 436, and a lumen 438 therebetween. The lumen 438 is sized to receive and slidably engage the sleeve 300 of the cannula assembly 210. An outer surface 440 of the sleeve 422 portion of the base 420 may include a substantially cylindrical shape. The lumen 438 of the sleeve 422 portion of the base 420 extends through the flange 424, thereby forming an aperture 442 in the flange.

A clamp receptacle 444 extends proximally from the proximal surface 428 of the flange 424. The clamp receptacle 444 includes at least one riser 446 extending from the proximal surface 428 of the flange 424 and a platform 448 extending from the at least one riser 446. In one aspect, the clamp receptacle 444 includes a first riser 450 and a second riser 452 with the platform 448 extending between the first and second risers. The platform 448 is shaped so as to not extend over the aperture 442 in the flange 424. In other words, the platform 448 provides clearance for the cannula assembly 210 such that the bolster 410 may slidably engage the cannula assembly without the platform interfering with the engagement. The platform 448 includes a distal surface 454 that is substantially parallel to the proximal surface 428 of the flange 424. As will be described below, the distance between the distal surface 454 of the platform 448 and the proximal surface 428 of the flange 424 is sufficient to receive the clamp mechanism 415 portion of the bolster 410. The distal surface 454 of the platform includes a substantially linear slot 456 extending radially therethrough. In one aspect, the base may be made of a polymeric material, such as a polycarbonate. However, it is contemplated that other materials, such as metals and composites, may be used.

Figure 24:
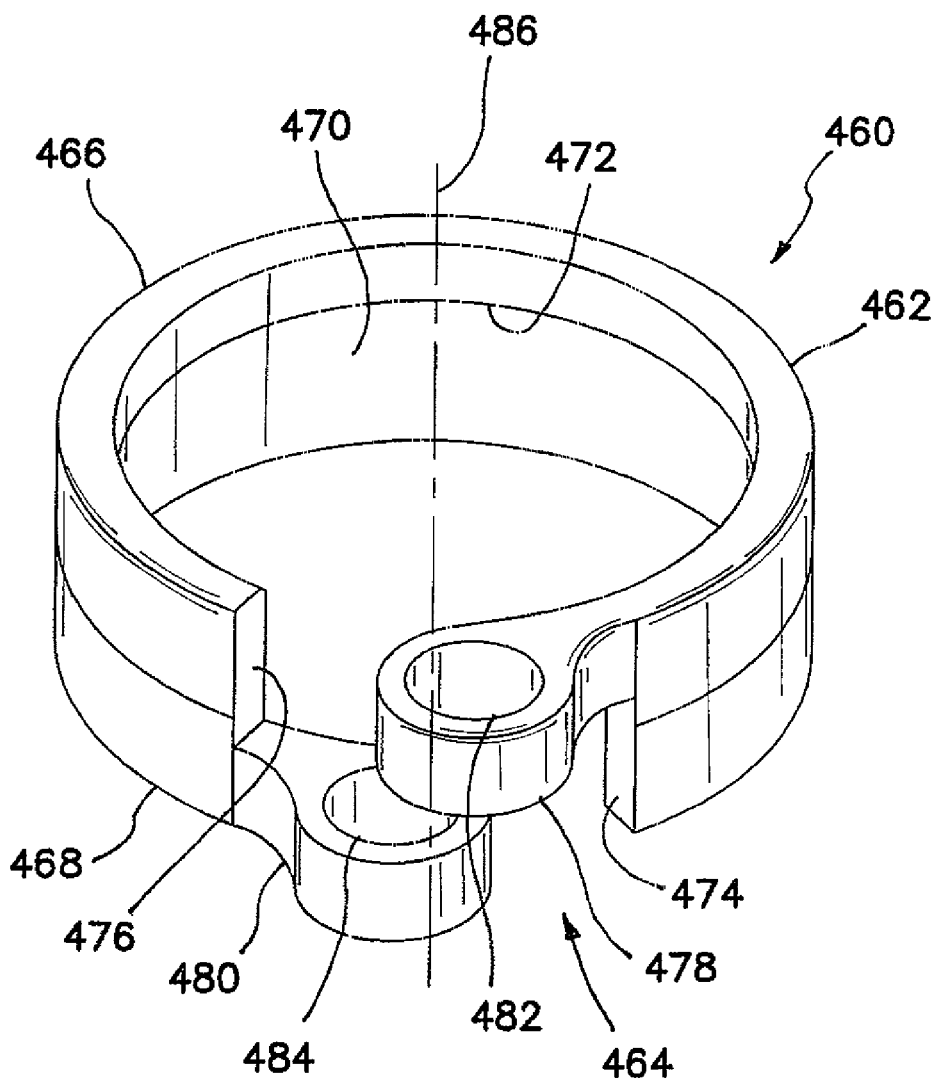
FIG. 24 is a perspective view of a collar portion of the bolster of FIG. 13.

Referring to FIG. 24, the collar 460 portion of the clamping mechanism 415 of the bolster 410 includes a substantially circumferential ring 462 defining a split 464. The collar 460 further includes a proximal end 466, a distal end 468, and an inner surface 470. The inner surface 470 of the collar 460 may include a counterbore configuration forming a ledge 472 therein. The split 464 in the collar 460 forms a first end 474 of the collar 460 and a second end 476 of the collar. The collar 460 is flexible in order to adjust the fit of the collar over the cannula assembly 210. More particularly, the first end 474 and the second end 476 of the collar may be brought closer together to create sufficient friction between the bolster 410 and the cannula assembly 210 to substantially fix the bolster in place along the length of the cannula assembly. The first end 474 and the second end 476 of the collar may also be spread apart to reduce or substantially eliminate the friction between the bolster 410 and the cannula assembly 210 so that the bolster may slide along the length of the cannula assembly.

To facilitate control of the distance between the first end 474 and the second end 476 of the collar 460, a first tab 478 extends from the first end 474 of the collar and a second tab 480 extends from the second end 476 of the collar. In one aspect, the first and second tabs 478, 480 may extend circumferentially from the first and second ends 474, 476, respectfully. In other aspects, the first and second tabs 478, 480 may extend tangentially or radially from the first and second ends 474, 476, respectfully, or in any other manner that is well known in the art. The first tab 478 includes a first aperture 482 extending longitudinally therethrough and the second tab 480 includes a second aperture 484 extending longitudinally therethrough. The first and second apertures 482, 484 extend substantially parallel to an axis 486 of the collar 460. As will be discussed below, the lever 500 interacts with the tabs 478, 480 to control the distance between the first and second ends 474, 476 of the collar 460. The collar may be made of a polymeric material, such as polycarbonate. However, it is contemplated that other materials, such as metals and composites, may be used.

Figure 25:
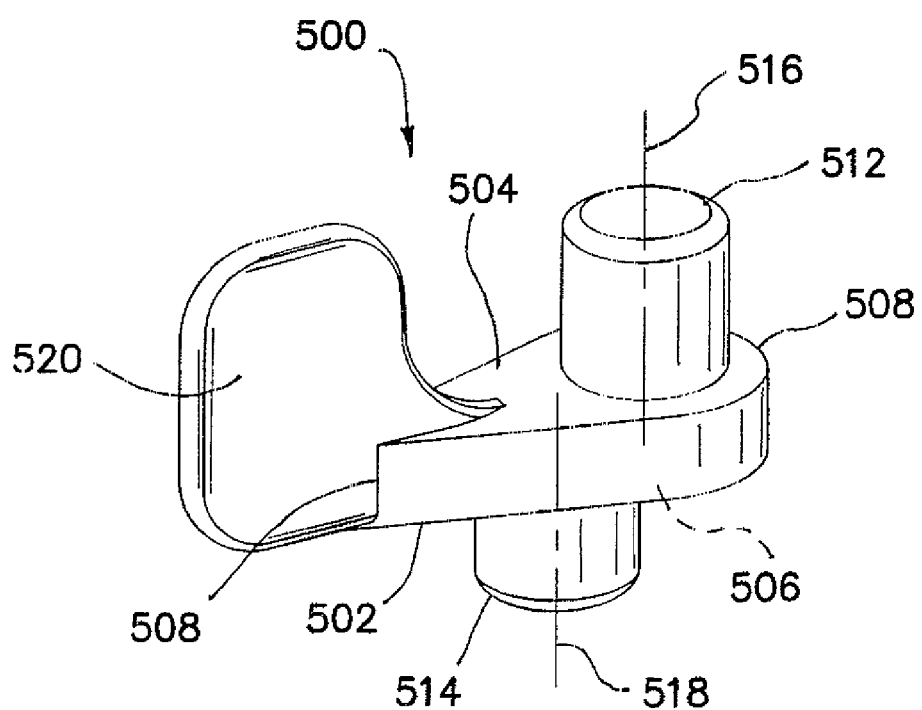
FIG. 25 is a perspective view of a lever portion of the bolster of FIG. 13.

Referring to FIG. 25, the lever 500 includes an arm 502 having a first, proximal surface 504, a second, distal surface 506, a first end 508 and a second end 510. The proximal and distal surfaces 504, 506 of the arm 502 are substantially parallel to each other. A substantially cylindrical first pin 512 extends proximally from the proximal surface 504 of the arm 502 proximate the first end 508 and a substantially cylindrical second pin 514 extends distally from the distal surface 506 proximate the first end. The first and second pins 512, 514 each extend substantially perpendicular from the proximal and distal surfaces 504, 506, respectively, of the arm 502. An axis 516 of the first pin 512 and an axis 518 of the second pin 514 are substantially parallel to each other, but are also offset from each other. In one aspect, the first pin 512 is closer to the first end 508 of the arm 502 than is the second pin 514. The peripheries of the first and second pins 512, 514 are sized to fit within the first and second apertures 482, 484, respectively, of the tabs 478, 480 of the collar 460. In one aspect, there may be a tab 520 positioned at the second end of the arm 502 to facilitate rotation of the lever 500 when it is assembled into the bolster 410.

Figure 26:
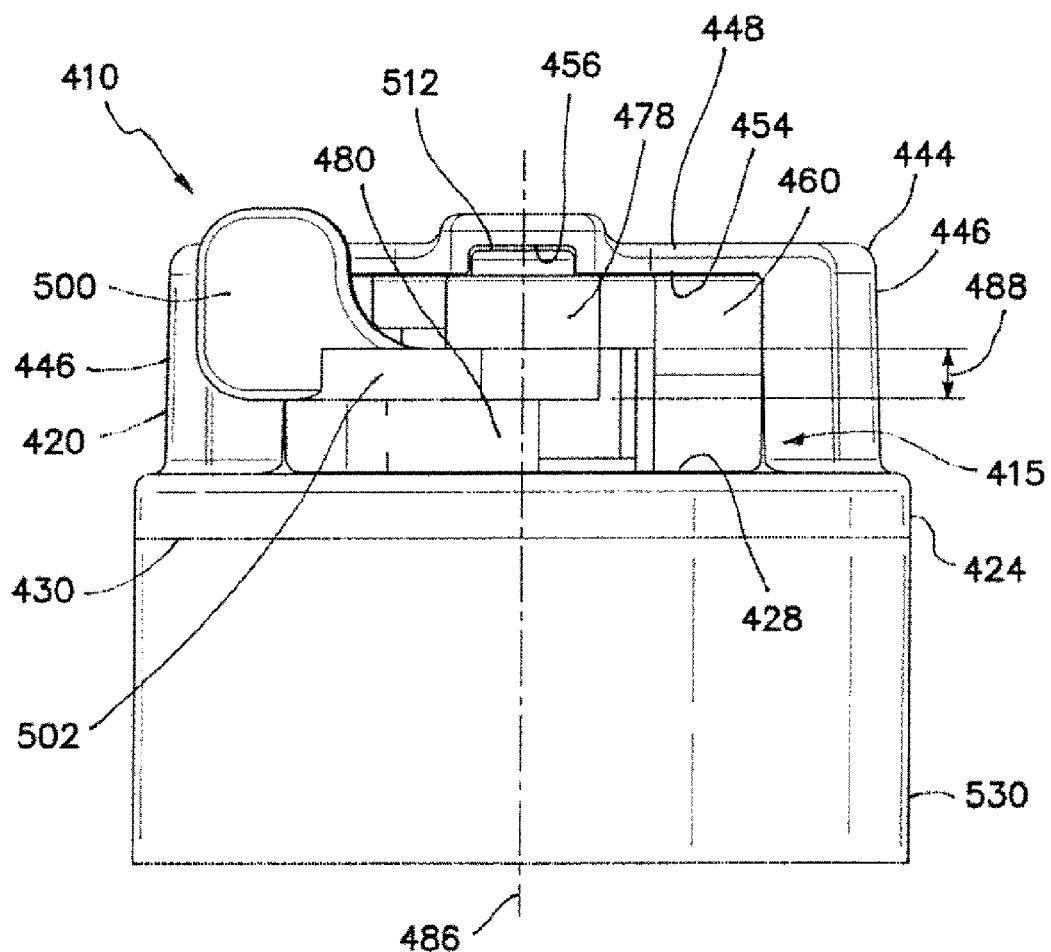
FIG. 26 is a side view of the bolster of FIG. 13.

Referring to FIG. 26, there is a space 488 between a distal surface of the first tab 478 of the collar 460 and a proximal surface of the second tab 480 of the collar. In one aspect, the distal surface of the first tab 478 and the proximal surface of the second tab 480 are substantially flat, substantially parallel to each other and substantially perpendicular to the axis 486 of the collar 460. The space 488 is sized to receive the arm 502 of the lever 500. The lever 500 is coupled to the collar 460 by manipulating the arm 502 of the collar into the space 488 between the first and second tabs 478, 480 of the collar and inserting the first pin 512 of the lever into the first aperture 482 (see FIG. 24) in the first tab 478 of the collar 460 and inserting the second pin 514 (see FIG. 25) of the lever into the second aperture 484 (see FIG. 24) in the second tab 480 of the collar. In this manner, the lever 500 is pivotally coupled to the collar 460. In one aspect, the first pin 512 of the lever is sufficiently long to extend beyond the proximal surface of the first tab 478 of the collar 460, while the second pin 514 is substantially flush or below flush with the distal surface of the second tab 480 of the collar.

Figure 27:
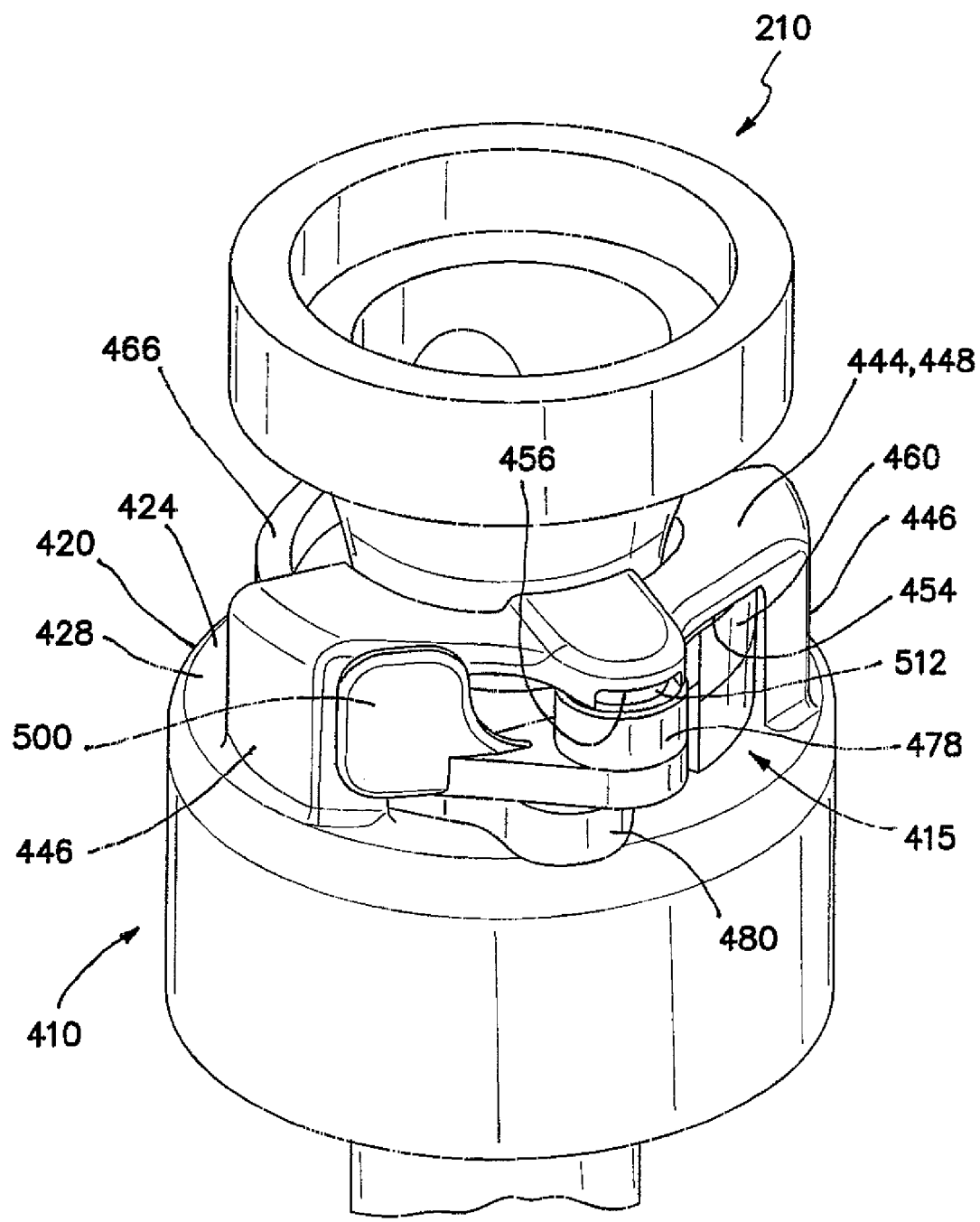
FIG. 27 is a perspective view of the bolster coupled to the sleeve portion of the balloon trocar.

With reference to FIG. 27 and continued reference to FIG. 26, to couple the clamping mechanism 415, including the collar 460 and lever 500, to the base 420, the collar and lever are inserted into the clamp receptacle 444 portion of the base. More particularly, the clamping mechanism 415 is inserted between the proximal surface 428 of the flange 424 portion of the base 420 and the distal surface 454 of the platform 448 of the clamp receptacle 444 portion of the base such that the collar 460 is nested between the flange 424, the platform 448, and the at least one riser 446 portion of the clamp receptacle 444. Further, the first and second tabs 478, 480 of the collar 460 and the first and second pins 512, 514 (see FIGS. 24 and 25) of the lever 500 are positioned between the proximal surface 428 of the flange 424 portion of the base 420 and the distal surface 454 of the platform 448. The distance between the proximal surface 428 of the flange 424 portion of the base 420 and the distal surface 454 of the platform 448 is sufficient for the clamp mechanism 415 to slidably engage within the clamp receptacle 444, yet also sufficiently low to maintain the lever 500 and collar 460 of the clamp mechanism 415 in an engaged relationship with each other during activation of the lever to maintain the clamping force of the collar against the cannula assembly 210. In one aspect, the first pin 512 of the lever 500, which extends proximally beyond the proximal surface of the first tab 478, is positioned within the slot 456 on the distal surface 454 of the platform 448 to facilitate maintaining the position of the first and second tabs 478, 480 of the collar 460 and the first and second pins 512, 514 of the lever 500 between the proximal surface 428 of the flange 424 portion of the base 420 and the distal surface 454 of the platform 448.

Referring to FIGS. 13 and 27, the bolster 410 is slidably mounted onto the cannula assembly 210 by inserting the distal end 256 of the cannula distally through the proximal end 466 of the collar 460, through the aperture 442 (see FIG. 23) of the flange 424 of the base 420, and through the sleeve 422 (see FIG. 23) of the base. The bolster 410 and cannula assembly 210 are slid relative to each other until the distal end 436 of the sleeve 422 (see FIG. 23) of the base 420 is proximal to the balloon 400 (see FIG. 19).

Figure 28:
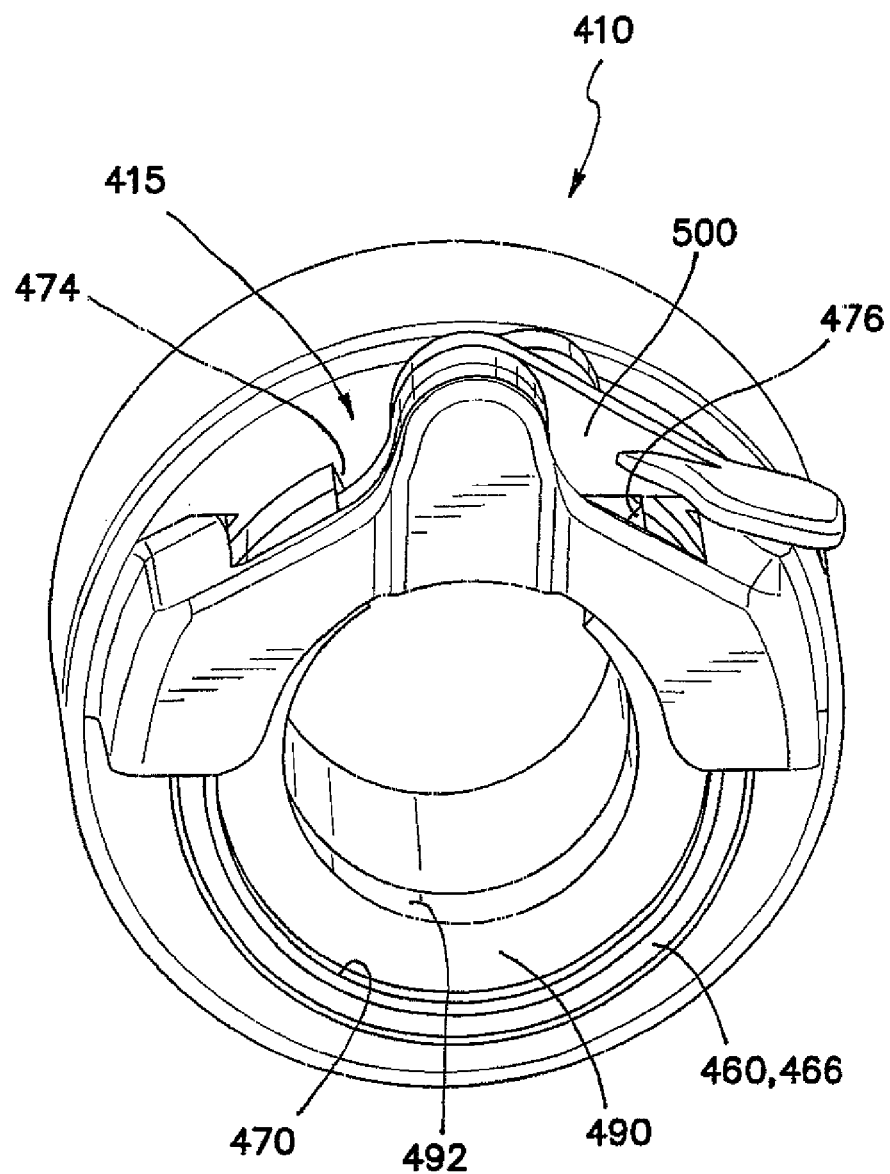
FIG. 28 is an end perspective view of the bolster of FIG. 13.

Referring to FIG. 28, when viewing the proximal end 466 of the collar 460 and lever 500 (looking distally), the distance between the first and second ends 474, 476 of the collar is at its maximum when the lever is in a first, clockwise position. Rotating the lever 500 in a counter clockwise direction moves the first and second ends 474, 476 of the collar 460 closer together, reducing the circumference of the collar and tightening the collar against the cannula assembly 210 (see FIG. 13). The change in circumference of the collar 460 as the lever 500 is rotated is caused by the offset between the first pin 512 and the second pin 514 of the lever (see FIG. 25). The circumference of the collar 460 is at its smallest when the lever is rotated about 180° from the first position. To facilitate the over-center lock design features of the clamping mechanism 415, the lever 500 is rotated from the first position more than about 180° to a second position. In this manner, as the lever 500 is rotating from the first position, the circumference of the collar 460 reduces until the lever has rotated about 180°, then expands slightly until the lever is positioned at the second position. With the lever 500 in the second position, higher pressure is initially required to rotate the lever away from the second position in a clockwise direction to the first position because the circumference of the collar 460 is reduced until the lever reaches the position that is about 180° from the first position. The higher pressure that is required protects against inadvertent release of the clamp mechanism 415. Although the clamp mechanism 415 was described in detail, those familiar in the art will recognize that other clamp mechanisms that are well known in the art may be used with satisfactory results.

In one aspect, the inner surface 470 of the collar clamps directly against an outer surface 322 of the sleeve 300 portion of the cannula assembly 210. In another aspect, the bolster 410 includes a compressible ring 490 positioned inside the collar 460. The ring 490 may be seated against the ledge 472 on the inner surface 470 of the collar 460. The inner surface 492 of the ring 490 is sized to permit the bolster 410 to slide along the cannula assembly 210 when the lever 500 is in the first position and to be compressed against the outer surface 322 of the sleeve 300 portion of the cannula assembly when the lever is in the second position. In this manner, the compressed ring 490 ensures that there is sufficient friction between the bolster 410 and the cannula assembly 210 when the lever is in the second position to maintain the position of the bolster along the cannula assembly. In one aspect, the ring 490 is made of an incompressible elastomeric material, such as silicone. In one aspect, the ring 490 is molded from a soft elastomeric material, such as a silicone having a hardness of about 40 Shore A durometer. Those familiar in the art will recognize that other materials that are well known in the art may be used and are contemplated to be within the scope of the invention.

With the bolster 410 mounted onto the cannula assembly, the ring 490 makes the collar 460 substantially self-centering around the cannula assembly 210. Having the first pin 512 of the lever 500 extending into the slot 456 on the distal surface 454 of the platform 448 substantially prevents the clamping mechanism 415 from rotating about the base 420 when the bolster is positioned on the cannula assembly 210 and the lever 500 is in the second position. This in turn substantially prevents the bolster 410 from rotating about the cannula assembly 210.

Referring again to FIGS. 13 and 26, to facilitate assistance of sealing the balloon 400 around the incision in the body wall, the bolster 410 includes a substantially annular gel pad 530 coupled to the distal surface 430 of the flange 424 portion of the base 420 and around the outer surface 440 of the sleeve 422 (see FIG. 23) portion of the base. In one aspect, the gel 530 is substantially incompressible. Since the gel pad 530 is substantially incompressible, it does not need to be as thick as the foam pads 180 of the prior art. Having a thinner pad provides the cannula assembly 210 with more usable length. The gel pad 530 may operate as a backup seal for the incision to help protect against leaks that might develop between the balloon and the inner surface of the body wall. In one aspect, the gel pad 530 may be between about 3.0-20.0 mm thick. However, in another aspect the gel pad 530 may be thicker to promote the sealing features of the gel pad.

The gel pad 530 is made of a gel and may be attached to, formed or integrated with the base 420. In one aspect, the gel is an elastomeric gel. In one aspect, the gel can be prepared by mixing a triblock copolymer with a solvent for the midblocks. The endblocks are typically thermoplastic materials such as styrene and the midblocks are thermoset elastomers such as isoprene or butadiene, e.g., Styrene-Ethylene-Butylene-Styrene (SEBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651. Once formed, the gel is substantially permanent and by the nature of the endblocks processable as thermoplastic elastomers henceforward. The mixture or slurry has a minimum temperature at which it becomes a gel, i.e., the minimum gelling temperature (MGT). This temperature in one aspect corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing a means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/ gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks will distribute and form more rapidly.

The various base formulas may also be alloyed with one another to achieve a variety of intermediate properties. For example, KRATON G1701X is a 70% SEB 30% SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics with the addition of a foaming agent that provide the desired qualities for the bolster to assist the balloon 400 to seal against the inner surface of the body wall 52. The silicone material may be of the types currently used for electronic encapsulation. The harder plastics may include PVC, Isoprene KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing boding sites or a surface charge. Additionally, oil based colorants may be added to the slurry to create gels of different colors.

In one aspect, the mixture/slurry used with the various embodiments of the bases 420 that are described herein are composed of 90% by weight of mineral oil and 10% by weight of KRATON G1651. From a thermodynamic standpoint, this mixture behaves similar to mineral oil. Mineral oil has a considerable heat capacity and therefore at about 130° C. it can take 3 or 4 hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect the gel may be air-cooled. Those familiar with the art will recognize that other cooling techniques that are well know in the art may be employed and are contemplated as within the scope of the present invention.

Many of the properties of the KRATON/oil mixture will vary with adjustments in the weight ratio of the components. In general, the greater the percentage of mineral oil, the less firm the mixture; the greater the percentage of KRATON, the more firm the mixture.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about 1.0 atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about 10%. Degassing the slurry helps reduce the potential of the finished gel to oxidize.

Degassing the slurry tends to make the resultant gel firmer. A degassed slurry composed of about 91.6% by weight of mineral oil and 8.4% by weight of KRATON G1651, an eleven-to-one ratio, results in a gel having about the same firmness as a gel made from a slurry that is not degassed composed of 90% by weight of mineral oil and 10% by weight of KRATON G1651, a nine-to-one ratio.

The gel in various aspects of the present invention may be gamma sterilized. As such, the relative or comparative simplicity of qualifying the sterilization process, for example of gamma versus ethylene oxide, of the gel and the device with the gel is desirable. However, under gamma sterilization large bubbles can form in the gel causing potential cosmetic or aesthetic issues in the sterilized devices. The bubbles are more than 99% room air and as such removal of the dissolved air in the slurry prior to forming the slurry into gel is performed. For example, the slurry may be degassed via vacuum as described above and turned into gel by heat. Bubbles may still form in the gel during gamma sterilization but disappear in a period of about 24 to 72 hours. In one aspect, the percentage of dissolved gas in the mineral oil at room temperature is about 10%. The removal of the air in the gel has an additional effect of making the gel firmer. This however is counterbalanced by the softening effect of gamma radiation on the gel during gamma sterilization.

In one aspect, if the gel is to be gamma sterilized, the gel may include about 90% mineral oil by weight and about 10% KRATON by weight. As stated above, degassing the slurry has the effect of making the gel firmer, however, the gamma radiation softens the gel to substantially the same firmness as a gel having about 90% mineral oil by weight and about 10% KRATON by weight that is not degassed or gamma sterilized.

In one aspect, cyanoacrylate, e.g., SUPERGLUE or KRAZY GLUE, may be used to bond or otherwise attach the gel pad 530 to the base 420. The glue may attach to either the rubber or styrene component of the tri-block and the bond is frequently stronger than the gel material itself.

In another aspect, a solvent is used to dissolve the plastics in the base 420 and the polystyrene in the gel. The solution of solvent is applied to the gel and base 420 in either a spray or dip form. In effect the solution melts both the plastic of the base as well as the polystyrene in the gel to allow a chemical bond to form between the two, which remains when the solvent evaporates.

Polyethylene can be dissolved in mineral oil and then applied to the gel. The mineral oil will not evaporate but will over time absorb into the gel and impart a polyethylene layer on the gel that may have beneficial properties.

In one aspect, the gel is cast into a mold containing the base 420. Adhesion between the gel pad 530 and the base 420 can be achieved by using KRATON polymer or a similar material in the base. The polystyrene in the gel is identified as achieving adhesion with polyphenylene oxide (PPO), polystyrene and others.

In the casting process, the gel pad 530 and the base 420 are heated to a temperature above about 130° C. and held at that temperature for several hours, e.g., about 3 to 4 hours. The temperature used is not sufficient to deform the base 420.

In one aspect, the base 420 comprises a polymer, e.g., polyethylene (PE). In one aspect, the polyethylene is a low-density polyethylene (LDPE) or high-density polyethylene (HDPE), or ultra high molecular weight polyethylene (UHM-WPE). In one aspect, the base 420 may be made of a polymer, such as polycarbonate and may be fabricated by methods including injection molding.

The gel includes mineral oil. PE has a higher molecular weight than mineral oil. PE is dissolved by mineral oil at high temperatures. As such, as the PE and mineral oil in the gel intermix as both are heated to and held at temperatures above about 130° C., a bond between the PE and gel is formed.

In one aspect, the base 420 is made of polycarbonate. The polycarbonate of the base does not form bonds with gel at 130° C. However during casting, by raising the temperature to about 150° C. for a few minutes, bonding occurs between the gel pad 530 and the base. As such, heating the gel and base to temperatures at which both the polystyrene of the gel and the polycarbonate are simultaneously beyond their melt points allows bonds to form between the gel pad 530 and the base 420. Alternatively, the gel and base may be heated to near or at the glass transition temperature of the polycarbonate base 420 to form the bond between the gel pad 530 and the base.

In one aspect, casting the gel pad 530 with the base 420 to form the bolster 410 includes placing the base into a casting mold. The mold may be made of aluminum, copper, brass, or other mold material having good heat dissipation properties. However, those familiar with the art will recognize that other mold materials having lower heat dissipation properties will produce acceptable parts and these are contemplated as within the scope of the present invention.

The mold having the base 420 is filled with the slurry. To facilitate filling voids in the mold with the slurry, the slurry may be preheated, for example, to about 52° C. (125° F.). Preheating the slurry to a temperature below the MGT reduces the viscosity of the slurry and allows the slurry to flow more easily. As stated above, the slurry may have been degassed in a vacuum. The slurry may be degassed again within the mold after the mold is filled to remove air that may have been introduced during the filling of the mold and to facilitate flow of the slurry into voids in the mold. Heat is applied to the mold having the base 420 and the slurry, such as in an oven, until the slurry attains a temperature of about 150° C. As stated above, the slurry turns into gel at about 120° C., however, at about 150° C., the gel can bond to a polycarbonate base 420. Depending on the material used to fabricate the base 420, bonding may take place at temperatures other than about 150° C. If the base 420 is fabricated of a material having a lower melting point than 120° C., then the gel pad 530 may be molded separately and then bonded to the base 420.

Once the temperature of the gel reaches about 150° C., the bolster 410 may be cooled, such as by air-cooling, cold-water immersion, or other cooling means that are well known in the art. At 150° C. the gel is soft and if it were distorted during cooling it would set with the distortion included. To reduce the likelihood of distorting the gel pad 530, the bolster 410 may be cooled within the mold. Cooling times may vary based on parameters including size and configuration of the mold, quantity of gel, temperature and quantity of cooling medium, cooling medium properties and the mold material. Whether cooling with air or water, the final properties of the gel are substantially the same. The bolster 410 is typically cooled to about ambient room temperature, but may be cooled to lower temperatures. The bolster 410 may be removed from the mold at any time after the gel has set.

When removed from the mold, the gel typically has a tacky surface. The gel pad 530 may be coated with a powder, such as cornstarch, to substantially reduce or eliminate the tackiness of the cured gel.

As stated above, in another aspect, the gel pad 530 may be molded separately from the base 420 and subsequently bonded to the base. In one aspect, the gel pad 530 may be molded into a slug. Since the gel 530 is being molded separate from the base 420, the slurry only needs to be heated until it reaches about 120° C. and completes the transformation from slurry into gel and the gel becomes substantially transparent. The gel pad 530 may then be placed onto the base 420. The gel pad 530 and base 420 are heated to a sufficient temperature for the polystyrene of the gel and the polymer of the base 420 to form bonds between the gel pad 530 and the base. Molding the gel pad 530 separately from the base 420 and heat bonding the gel pad to the base at a later time is especially useful when the base is made of a material that has a lower melting temperature than the MGT. In such situations, the gel pad 530 can be molded first and heat bonded to the base 420 without melting the base.

During a surgical procedure in which the balloon trocar 200 of the present invention may be used, a surgeon may gain access to the abdominal cavity 52 through the abdominal wall 50 by using the "Hassan" or "cut-down" technique. However, use of the Hassan or cut-down technique often leaves a defect larger than the trocar that will be located through the incision. Therefore, it is necessary to provide a means to seal the incision after the trocar has been inserted in order to insufflate the patient's abdominal cavity. The balloon trocar 200 of the present invention provides such sealing means.

Figure 17:
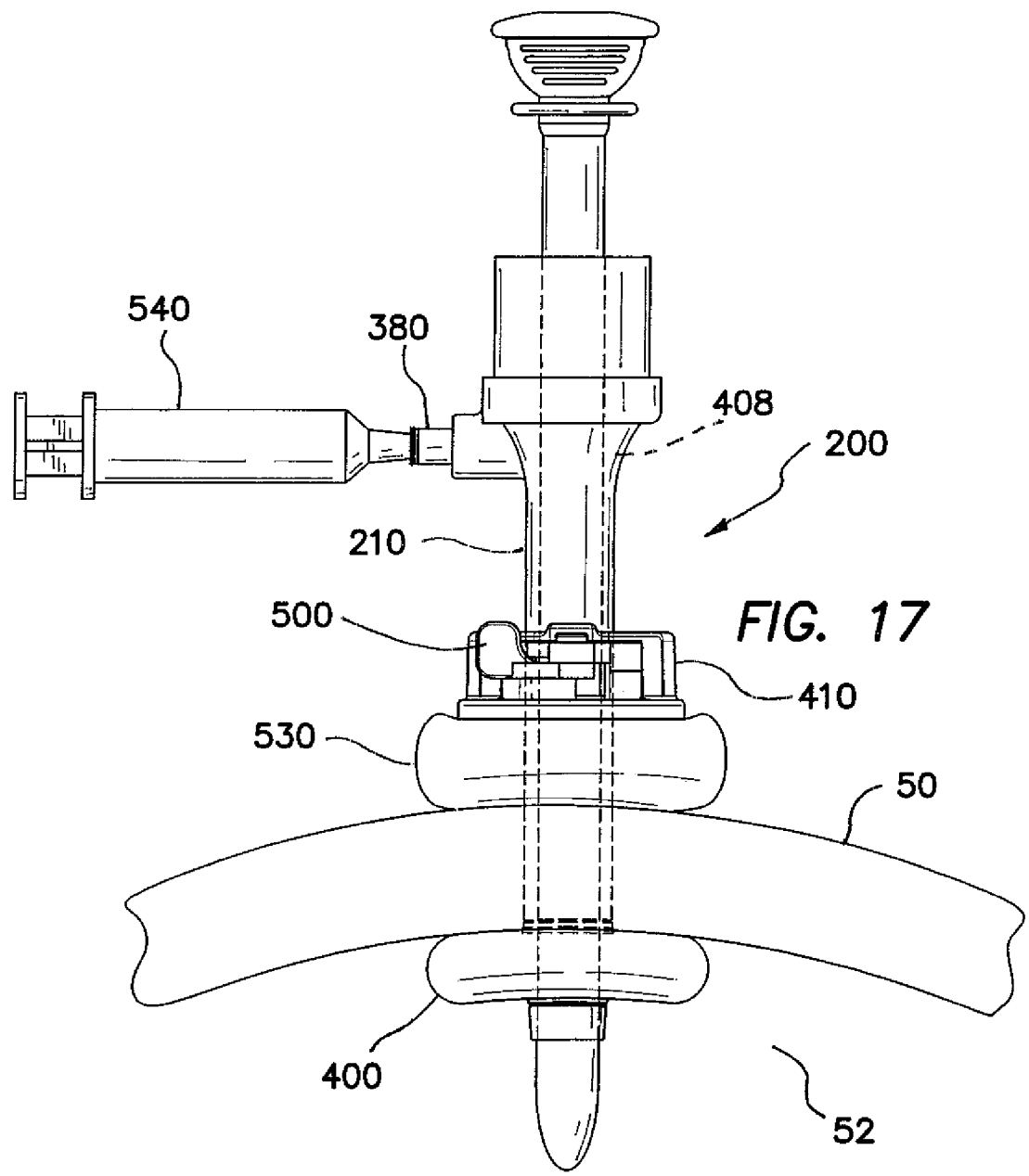
FIG. 17 illustrates a cannula assembly of the present invention placed through a body wall.

Referring to FIG. 17, once an incision is made in the body wall 50 to gain entry to the body cavity 52, such as the abdominal cavity, the distal end of the balloon trocar 200 is inserted through the incision until the balloon 400 at the distal portion of the cannula assembly 210 is within the body cavity. A syringe 540 may be inserted into the port 380 and used to inflate the balloon 400 by injecting gas or fluid into the chamber 408. To seal the balloon 400 against the interior surface of the body wall 50, the bolster 410 may be advanced distally along the cannula while pulling the balloon trocar 200 proximally until the inflated balloon is compressed against the inner surface of the body wall 50 and the gel pad 530 is compressed against the outer surface of the body wall. The lever 500 may be rotated to apply clamping force from the clamp mechanism 415 onto the outer sleeve 300 to maintain the position of the bolster on the cannula assembly 210, thereby maintaining compression of the balloon 400 against the interior surface of the body wall 50 and compression of the gel pad 530 against the exterior surface of the body wall. With the incision sealed, the body cavity 52, such as the abdominal cavity, may be insufflated with $CO_2$ or a similar gas. To deflate the balloon 400 for removal of the balloon trocar 200 from the body cavity 52, the plunger 384 (see FIG. 18) within the port 380 may be depressed to release the gas or fluid from the balloon. The syringe 540 may be used to depress the plunger 384 within the port 380 and the syringe used to pull the gas or fluid from the chamber 408, thereby deflating the balloon 400.

Figure 29:
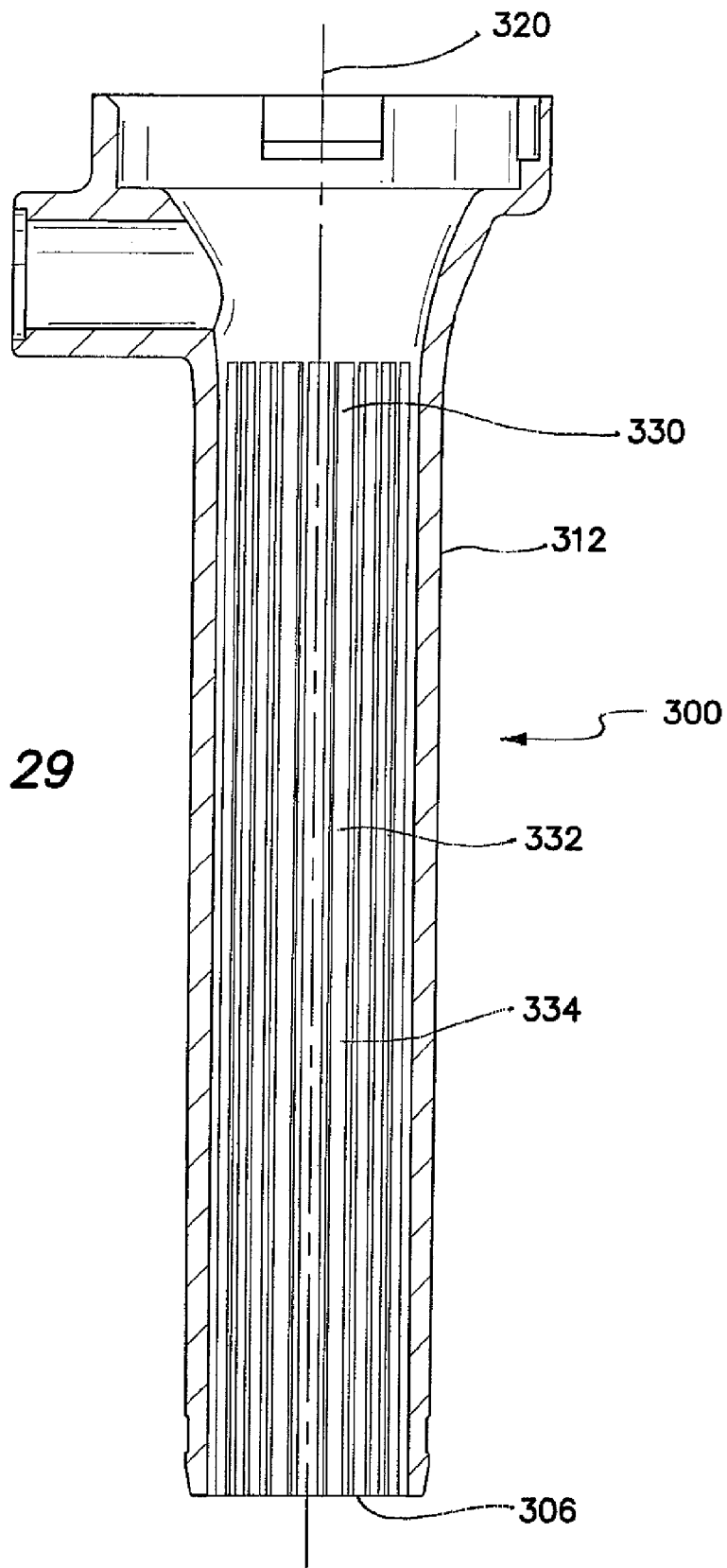
FIG. 29 is a plan view, in cross section of a sleeve portion of the balloon trocar of FIG. 13 with an inner surface of the sleeve including channels.

Referring to FIG. 29, an inner surface 330 of the outer sleeve 300 may include a plurality of channels 332 extending along the length of the outer sleeve from substantially the proximal end of the distal portion 312 of the outer sleeve distally to the distal end 306 of the outer sleeve. The channels 332 are similar to the channels 268 described for the outer surface of the cannula 250. The plurality of channels 332 on the inner surface 330 of the outer sleeve 300 is adapted to facilitate the flow of gasses or fluids therethrough. In one embodiment, the plurality of channels 332 on the inner surface 330 of the outer sleeve 300 may include a plurality of substantially longitudinal grooves 334 that are substantially parallel to the longitudinal axis 320 of the outer sleeve. With the plurality of channels 332 on the inner surface 330 of the sleeve 300, the sleeve 300 may be used with either the cannula 250 having a plurality of channels 268 on the outer surface of the cannula to further increase the flow of gasses or fluids between the sleeve and cannula, or a cannula having a substantially smooth outer surface.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of many embodiments. Those skilled in the art will envision other modifications within the scope and spirit of the present invention as defined by the following claims.

The invention claimed is:

1. A balloon trocar system comprising:
a cannula assembly comprising:
  a cannula having a proximal end, a distal end, a lumen extending between the proximal end and the distal end, a proximal portion having a first, larger periphery, a distal portion having a second, smaller periphery, and an annular groove on an outer surface of the distal portion of the cannula toward the distal end of the cannula;
  an outer sleeve comprising:
    a substantially longitudinal tube having a proximal end, a distal end, a lumen extending between the proximal end and the distal end, a proximal portion having a first, larger periphery, a distal portion having a second, smaller periphery; and
    a balloon extending distally from the distal end of the longitudinal tube; and
  wherein the outer sleeve is positioned around the cannula such that the proximal portion of the longitudinal tube of the outer sleeve is coupled to the proximal portion of the cannula and the balloon is coupled with the annular groove of the cannula to define a substantially closed chamber between the outer surface of the cannula, an inner surface of the outer sleeve from the proximal end of the longitudinal tube to the annular groove of the cannula;
a trocar seal removably couplable to the proximal end of the cannula; and
an obturator comprising an elongate shaft extending along a substantially longitudinal axis between a proximal end and a distal end, the obturator positionable through the trocar seal and lumen of the cannula such that the proximal end of the obturator is proximal to the trocar seal and the distal end of the obturator is distal to the distal end of the cannula.

2. The balloon trocar system of claim 1, wherein the elongate shaft of the obturator has a first periphery sized to be slidable within the lumen of the cannula and wherein the obturator further comprises:
a handle positioned at the proximal end of the elongate shaft, the handle having a second periphery larger than the first periphery of the elongate shaft; and
a distal tip at the distal end of the elongate shaft, the distal tip having a prolate spheroid shape.

3. The balloon trocar system of claim 1, wherein the balloon is inflatable from a deflated condition in which the balloon is foldable onto the cannula and longitudinal tube to an inflated configuration having a relatively large profile.

4. The balloon trocar system of claim 3, wherein the balloon has a toroid profile in the inflated configuration.

5. The balloon trocar system of claim 1, wherein the lumen of the longitudinal tube is configured to provide minimal space between the distal portion of longitudinal tube and the distal portion of the cannula.

6. The balloon trocar system of claim 1, wherein the balloon is substantially flush with the cannula at the annular groove.

7. A cannula assembly comprising:
a cannula having a proximal end, a distal end, a lumen extending between the proximal end and the distal end, a proximal portion having a first, larger periphery, a distal portion having a second, smaller periphery, a transition region between the proximal portion and the distal portion, a plurality of longitudinal channels extending along the length of the cannula, and an annular groove on an outer surface of the distal portion of the cannula distal of the plurality of longitudinal channels adjacent the distal end of the cannula;
an outer sleeve comprising:
  a substantially longitudinal tube having a proximal end, a distal end, a lumen extending between the proximal end and the distal end, a proximal portion having a first, larger periphery, a distal portion having a second, smaller periphery, and a transition region between the proximal portion and the distal portion, the lumen of the sleeve being configured to accept the cannula such that the proximal portion of the longitudinal tube fits over and sealingly engages with the proximal portion of the cannula and the distal portion of the longitudinal tube fits over the distal portion of the cannula providing minimal space therebetween; and
  a balloon extending distally from the distal end of the longitudinal tube and coupled with the annular groove of the cannula such that a closed chamber is defined by a space between the outer surface of the cannula and an inner surface of the outer sleeve extending from the sealing engagement of the proximal portion of the cannula and the proximal portion of the longitudinal tube distally to the coupling of the balloon and the annular groove; and
an inflation port providing a fluid pathway for fluid to be introduced and removed from the closed chamber.

8. The cannula assembly of claim 7, wherein the inflation port comprises a check valve having a spring-loaded plunger.

9. The cannula assembly of claim 8, wherein the check valve further comprises a luer lock.

10. The cannula assembly of claim 7, wherein the inflation port is disposed on the outer sleeve.

11. The cannula assembly of claim 7, wherein the inflation port is disposed distal of the sealing engagement between the proximal portion of the longitudinal tube and the proximal portion of the cannula.

12. The cannula assembly of claim 7, wherein the lumen of the longitudinal tube is configured to define a gap between the transition region of the longitudinal tube and the transition region of the cannula, wherein the gap is larger than the space between the distal portion of the longitudinal tube and the distal portion of the cannula.

13. The cannula assembly of claim 7, wherein the cannula has a generally tubular wall with a thickness and wherein the plurality of longitudinal channels are formed recessed into the generally tubular wall of the cannula such that the thickness of the wall is not increased by the plurality of longitudinal channels.

14. The cannula assembly of claim 7, further comprising an O-ring positioned between the proximal portion of the longitudinal tube and the proximal portion of the cannula to provide the sealing engagement therebetween.

15. A cannula assembly comprising:
    a cannula having a proximal end, a distal end, a lumen extending between the proximal end and the distal end, and an annular groove on an outer surface of the cannula adjacent the distal end;
    a sleeve positioned over the cannula, the sleeve comprising:
        a substantially longitudinal tube having a proximal end, a distal end, and a lumen extending between the proximal end and the distal end;
        a balloon extending distally from the distal end of the longitudinal tube; and
        wherein the sleeve is positioned around the cannula such that the proximal end of the longitudinal tube is coupled to the cannula adjacent the proximal end of the cannula and the balloon is fixed in place within the annular groove of the cannula such that the balloon is substantially flush with the cannula at the annular groove; and
    a bolster slidably adjustable along the length of the cannula and the sleeve proximal to the balloon.

16. The cannula assembly of claim 15, further comprising thread wound around the balloon at the annular groove to force the balloon into the annular groove.

17. The cannula assembly of claim 15, wherein the bolster comprises:
    a base having a lumen sized to receive and slidingly engage the sleeve;
    a clamping mechanism coupled to the base, the clamping mechanism actuatable between a first position in which the bolster is slidable relative to the cannula and a second position in which the clamping mechanism maintains a location of the bolster relative to the sleeve; and
    a gel pad coupled to the base.

18. The cannula assembly of claim 17, wherein the gel pad comprises a substantially incompressible gel material.

19. The cannula assembly of claim 17, wherein the base comprises a clamp receptacle, and wherein the clamping mechanism comprises:
    a collar positioned in the clamp receptacle, the collar having a first end, a second end, and an inner surface; and
    a lever coupled to the first end and the second end of the collar, the lever pivotable between a first position in which the first end and the second end of the collar are spread apart to allow the bolster to slide along the sleeve and a second position in which the first end and the second end of the collar are closer together to fix the bolster in place relative to the sleeve.

* * * * *